US009205156B2

(12) United States Patent
Mishani et al.

(10) Patent No.: US 9,205,156 B2
(45) Date of Patent: Dec. 8, 2015

(54) MOLECULAR IMAGING AGENTS

(75) Inventors: Eyal Mishani, Mevasseret Tzion (IL); Ohad Ilovich, Kadima (IL); Hana Billauer, Jerusalem (IL); Sharon Dotan, Kfar Saba (IL); Haim Danenberg, Jerusalem (IL); Moshe Bocher, Jerusalem (IL); Galith Abourbeh, Jerusalem (IL); Nanette Freedman, Jerusalem (IL)

(73) Assignee: HADASIT MEDICAL RESEARCH SERVICES & DEVELOPMENT LIMITED, Jerusalem (IL)

( * ) Notice: Subject to any disclaimer, the term of this patent is extended or adjusted under 35 U.S.C. 154(b) by 217 days.

(21) Appl. No.: 13/116,804

(22) Filed: May 26, 2011

(65) Prior Publication Data

US 2011/0293519 A1 Dec. 1, 2011

Related U.S. Application Data

(60) Provisional application No. 61/348,983, filed on May 27, 2010.

(51) Int. Cl.
A61K 51/00 (2006.01)
A61M 36/14 (2006.01)
A61K 51/04 (2006.01)
C07C 211/63 (2006.01)
C07C 211/64 (2006.01)

(52) U.S. Cl.
CPC ........... *A61K 51/0406* (2013.01); *C07C 211/63* (2013.01); *C07C 211/64* (2013.01)

(58) Field of Classification Search
CPC . A61K 51/0406; C07C 211/63; C07C 211/64
USPC ........................................................ 424/1.85
See application file for complete search history.

(56) References Cited

U.S. PATENT DOCUMENTS 4,446,123 A * 5/1984 Woo .............................. 424/1.65
7,112,318 B2 9/2006 Madar et al.

OTHER PUBLICATIONS

Fukuda et al. Eur. J. Nucl. Med. (1986) 11:478-483.*
Zheng et al. Bioorg. Med. Chem. Lett. 13 (2003) 1787-1790.*
Ilovich, et al., "Novel and Simple Carbon-11-Labeled Ammonium Salts as PET Agents for Myocardial Perfusion Imaging", Mol Imaging Biol, published online: May 18, 2010.
Kim, et al., "In vivo targeting of ERG potassium channels in mice and dogs by a positron-emitting analogue of fluoroclofilium", Experimental and Molecular Medicine, vol. 37, No. 4, pp. 269-275, (2005).
Huang, et al., "In Vivo Stability and Distribution of [131I]Iodomethyl Trimethylammonium Chloride: Concise Communication", J Nucl Med, vol. 21, No. 7, pp. 679-681, (1980).
Burns, et al., "4-[125I] Iodophenyltrimethylammonium Ion, an Iodinated Acetylcholinesterase Inhibitor with Potential as a Myocardial Imaging Agent", J Nucl Med, vol. 21, No. 9, pp. 875-879, (1980).
Madar, et al., "Characterization of Uptake of the New PET Imaging Compound 18F-Fluorobenzyl Triphenyl Phosphonium in Dog Myocardium", J Nucl Med, vol. 47, pp. 1359-1366, (2006).
Yu, et al., "Assessment of 18F-labeled mitochondrial complex I inhibitors as PET myocardial perfusion imaging agents in rats, rabbits, and primates", Eur J Nucl Med Mol Imaging, vol. 36, pp. 63-72, (2009).
Madar, et al., "Characterization of membrane potential-dependent uptake of the novel PET tracer 18F-fluorobenzyl triphenylphosphonium cation", Eur J Nucl Med Mol Imaging, vol. 34, pp. 2057-2065, (2007).
Marshall, et al., "Kinetic Analysis of 18F-Fluorodihydrorotenone as a Deposited Myocardial Flow Tracer: Comparison to 201Tl", J Nucl Med, vol. 45, No. 11, pp. 1950-1959, (2004).
Crouzel, et al., "Recommendations for a Practical Production of [11C]methyl Iodide", Appl. Radiat. Isot., Int. J. Radiat. Appl. Instrum. Part A, vol. 38, No. 8, pp. 601-603, (1987).
Russell, et al., "Nuclear Cardiology: Present and Future", Curr Probl Cardiol, vol. 31, pp. 557-629, (2006).
Underwood, et al., "Myocardial perfusion scintigraphy and cost effectiveness of diagnosis and management of coronary heart disease", Heart, vol. 90 (Suppl V), pp. v34-v36, (2004).
Hachamovitch, et al., "Value of Stress Myocardial Perfusion Single Photon Emission Computed Tomography in Patients With Normal Resting Electrocardiograms: An Evaluation of Incremental Prognostic Value and Cost-Effectiveness", Circulation, vol. 105, pp. 823-829, (2002).
Marcassa, et al., "Clinical value, cost-effectiveness, and safety of myocardial perfusion scintigraphy: a position statement", European Heart Journal, vol. 29, pp. 557-563, (2008).
Beller, "First Annual Mario S. Verani, MD, Memorial Lecture: Clinical value of myocardial perfusion imaging in coronary artery disease", J Nucl Cardiol, vol. 10, pp. 529-542, (2003).
Aerts, et al., "Metabolism of no-carrier-added 2-[18F]fluoro-L-tyrosine in rats", BMC Medical Physics, vol. 8, No. 4, pp. 1-7, (2008).
Mazière, et al., "In Vivo Characterization Of Myocardium Muscarinic Receptors by Positron Emission Tomography", Life Sciences, vol. 29, pp. 2391-2397, (1981).
Wang, et al., "Facile synthesis of new carbon-11 labeled conformationally restricted rivastigmine analogues as potential PET agents for imaging AChE and BChE enzymes", Applied Radiation and Isotopes, vol. 66, pp. 506-512, (2008).
Schillaci, et al., "18F-choline PET/CT physiological distribution and pitfalls in image interpretation: experience in 80 patients with prostate cancer", Nucl Med Commun, vol. 31, p. 39-45, (2010).

(Continued)

*Primary Examiner* — Michael G Hartley
*Assistant Examiner* — Sean R Donohue
(74) *Attorney, Agent, or Firm* — Vorys, Sater, Seymour and Pease LLP

(57) ABSTRACT

Provided is radiolabeled ammonium salts and uses thereof as myocardial perfusion agents in molecular imaging.

2 Claims, 15 Drawing Sheets

(56) References Cited

OTHER PUBLICATIONS

Kil, et al., "Synthesis and positron emission tomography studies of carbon-11-labeled imatinib (Gleevec)", Nuclear Medicine and Biology, vol. 34, pp. 153-163, (2007).

Studenov, et al., "Synthesis and properties of 18F-labeled potential myocardial blood flow tracers", Nuclear Medicine and Biology, vol. 28, pp. 683-693, (2001).

Apolo, et al., "Novel Tracers and Their Development for the Imaging of Metastatic Prostate Cancer", J Nucl Med, vol. 49, pp. 2031-2041, (2008).

Degrado, et al., "Synthesis and Evaluation of 18F-labeled Choline as an Oncologic Tracer for Positron Emission Tomography: Initial Findings in Prostate Cancer", Cancer Res, vol. 61, pp. 110-117, (2000).

Degrado, et al., "Synthesis and Evaluation of 18F-Labeled Choline Analogs as Oncologic PET Tracers", J Nucl Med, vol. 42, pp. 1805-1814, (2001).

Herrero, et al., "Comparison of 1-11C-Glucose and 18F-FDG for Quantifying Myocardial Glucose Use with PET", The Journal of Nuclear Medicine, vol. 43, No. 11, pp. 1530-1541, (2002).

Jonson, et al., "Investigations into tumor accumulation and peroxisome proliferator activated receptor binding by F-18 and C-11 fatty acids", Nuclear Medicine and Biology, vol. 29, pp. 211-216, (2002).

Torstenson, et al., "A Comparison of 11C-Labeled L-DOPA and L-Fluorodopa as Positron Emission Tomography Tracers for the Presynaptic Dopaminergic System", Journal of Cerebral Blood Flow and Metabolism, vol. 19, pp. 1142-1149, (1999).

Volkow, et al., "Mechanism of action of methylphenidate: Insights from PET imaging studies", Journal of Attention Disorders, vol. 6, Supplement Jan. 2002, pp. S-31-S-43, (2002).

\* cited by examiner

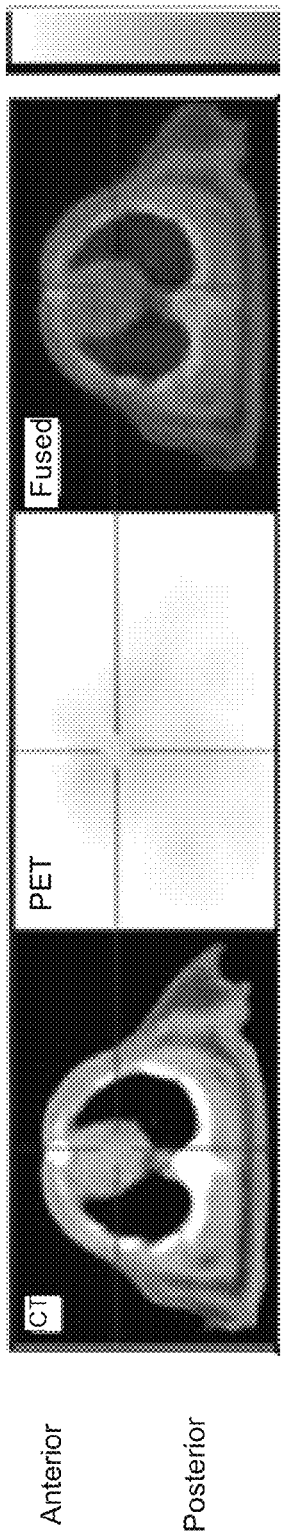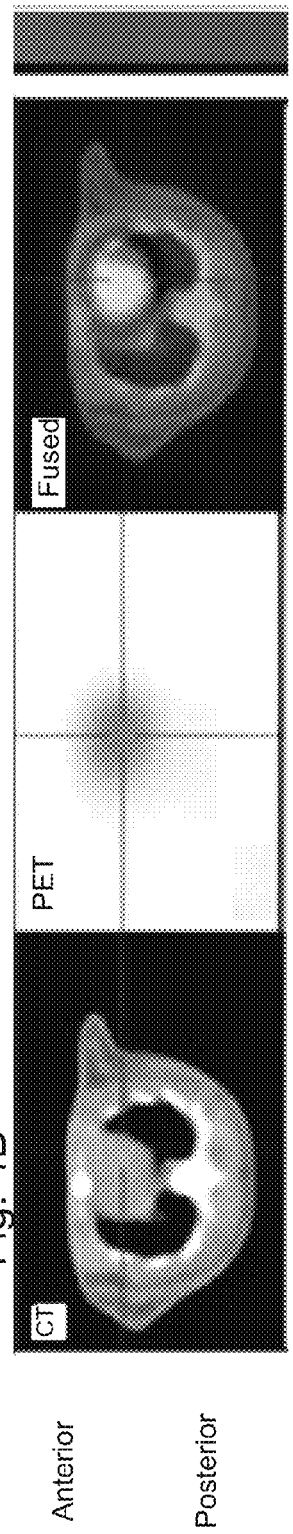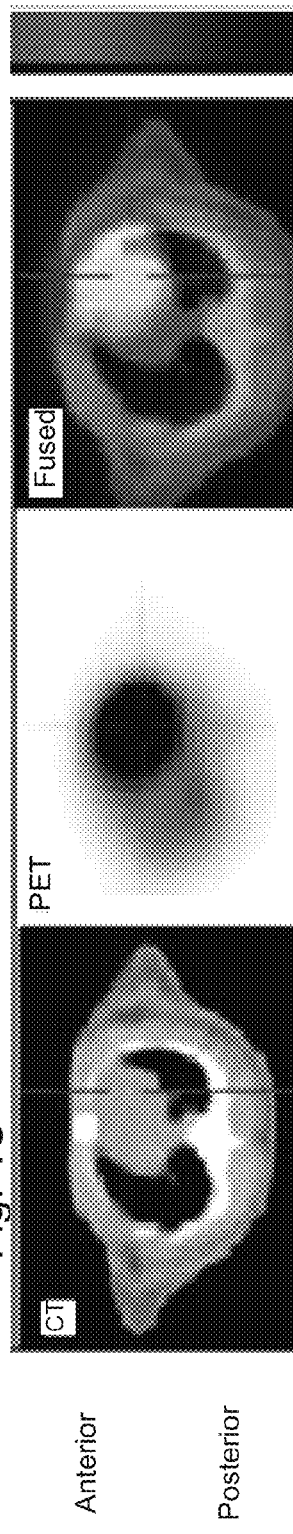

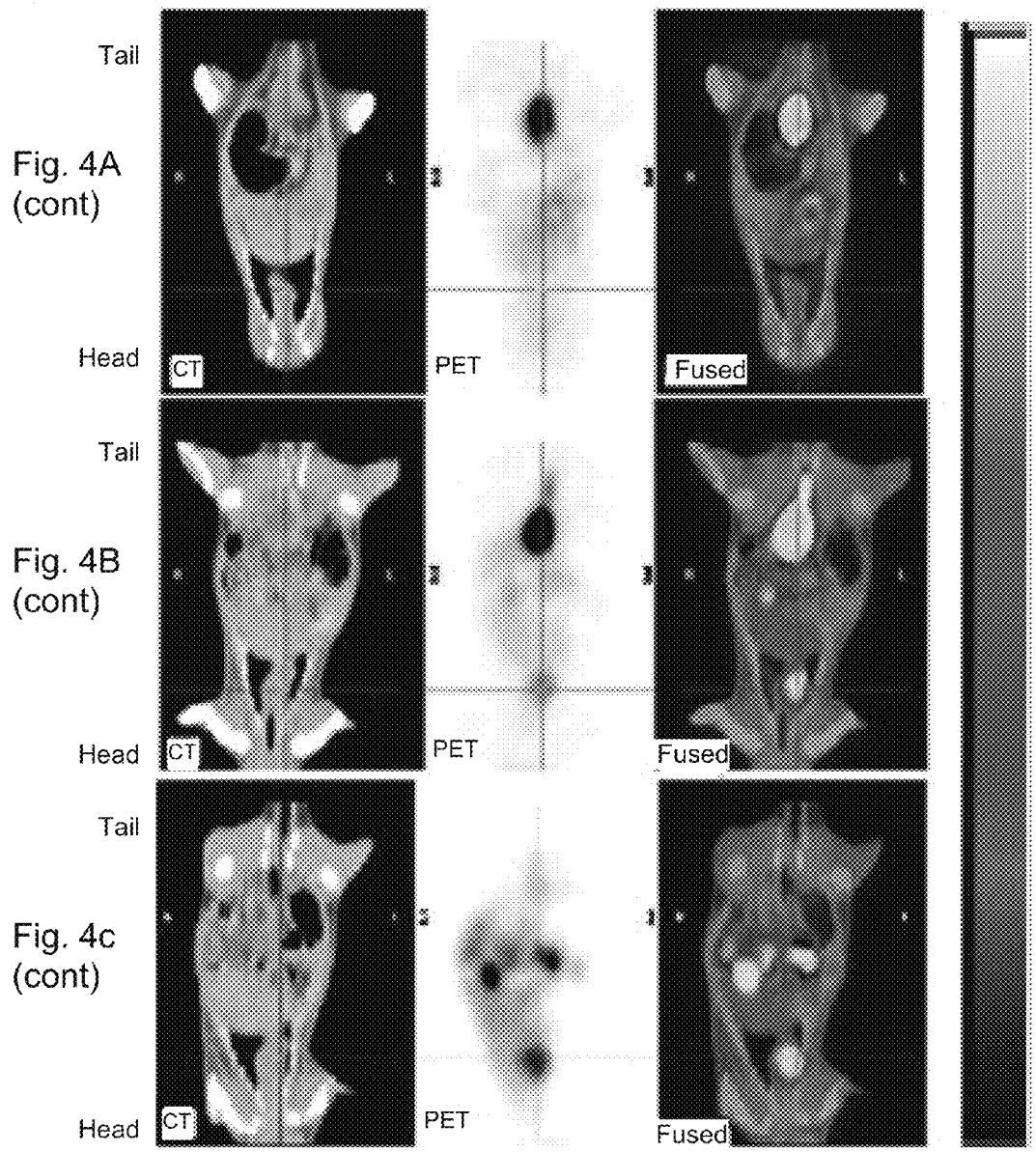

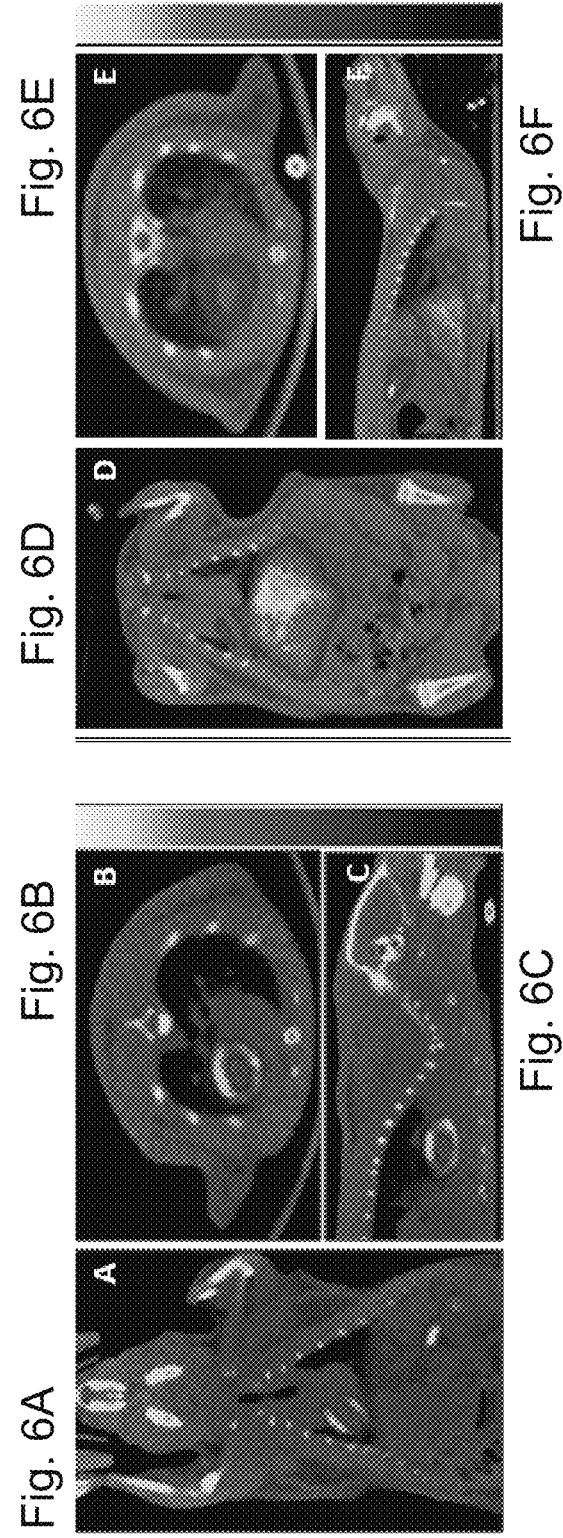

US 9,205,156 B2

MOLECULAR IMAGING AGENTS

This is a Non-Provisional Application claiming the benefit under 35 U.S.C. §119(e) of U.S. Provisional Application No. 61/348,983, filed on May 27, 2010, the content of each of which is hereby incorporated by reference in its entirety.

FIELD OF THE INVENTION

The present invention generally relates to labeled ammonium salts and uses thereof as myocardial perfusion agents in molecular imaging.

BACKGROUND OF THE INVENTION

Myocardial perfusion imaging (MPI) is the most common tool for non-invasively evaluating ischemia in patients with suspected coronary artery disease (CAD). This technique contributes substantially to the risk-stratification of CAD patients, in terms of their likelihood to encounter coronary events and cardiac death. Therefore, MPI provides valuable information which assists clinical decision-making with regard to medical treatment and intervention. There is a growing and consistent evidence that gated MPI provides additional clinically useful data towards patient risk stratification, by enabling the assessment and comparison of left ventricular function during both post-stress and rest conditions.

Current data suggest that positron emission tomography (PET) MPI is a powerful modality for diagnosing obstructive CAD, and appears to provide better diagnosis than single photon emission computed tomography (SPECT); this is primarily related to PET technological advantages, such as higher count sensitivity, better spatial resolution and more accurate attenuation correction. The ability to quantify myocardial perfusion in absolute values is an added advantage of PET over SPECT, particularly in multivessel CAD.

Despite the known advantages of PET, SPECT tracers and [$^{99m}$Tc]-MIBI, in particular, are more prevalent in clinical practice. This is primarily due to the two following reasons: (i) the use of SPECT radiopharmaceuticals is logistically easier, and tracer dose price is usually lower than the respective cyclotron-produced PET pharmaceuticals, and (ii) existing PET MPI probes have short physical half lives, which require in-house production, and more importantly, have suboptimal pharmacokinetic profiles, which most likely withhold the shift of nuclear cardiology from SPECT to the superior PET modality.

Nevertheless, in light of the potential contribution of PET to the field of MPI, increasing efforts were invested into the development of new PET MPI probes.

In the last decade, a wealth of effort has been invested into the development of optimal PET myocardial perfusion agents. Several fluorine-18 labeled myocardial flow tracers were reported in the literature. [$^{18}$F]RP1004 [1], [$^{18}$F]FBnTP [2, 3] and [$^{18}$F]FDHR [3] base their cardiac accumulation on interactions with mitochondria which are plentiful in the heart muscle. The longer half-life of fluorine-18 enables extensive radiochemical transformations, extended PET scan times and commercial distribution. A wait of a period of four to five half-lives is ideally required between equal doses administered at rest and stress tests to allow for radioactivity from the first injection to decay to a point where it does not interfere significantly with the later scan. Fluorine-18 based tracers may prevent performance of both scans during a single day or at least require several hours stay interval while using an initial low dose followed by a high dose later, similarly to a "one-day protocol" used with $^{99m}$Tc-labled SPECT flow tracers.

Several publications discuss the utilization of radiolabled tracers in molecular imaging techniques such as PET.

REFERENCES

[1] Yu M, et al., (2009), *Eur j nuc med mol imag*, 36(1):63-72.
[2] Madar I, et al., (2007), *Eur j nuc med mol imag*, 34(12): 2057-2065.
[3] Madar I, et al., (2006), *J Nucl Med*, 47(8):1359-1366.
[4] Marshall R C, et al., (2004), *J Nucl Med* 45(11):1950-1959.
[5] Beller G A (2003), *J Nucl Cardiol*, 10(5):529-542.
[6] Hachamovitch R, et al. (2002), *Circulation*, 105(7):823-829.
[7] Marcassa C, et al. (2008), *Eur Heart J*, 29(4):557-563.
[8] Russell R R, 3rd, Zaret B L (2006), *Nuclear cardiology: present and future. Curr Probl Cardiol*, 31(9):557-629.
[9] Underwood S R, et al. (2004), *Heart* 90 Suppl, 5v34-36.
[10] Studenov R and Berridge M S, (2001), *Nuclear Medicine and Biology*, Volume 28, Issue 6, Pages 683-693.
[11] Aerts J J, et al., (2008), *BMC Medical Physics*, 8:4.
[12] DeGrado T R., et al. (2001) *Cancer Res*, 1; 61(1):110-7.
[13] Schillaci O, et al., (2010) *Nucl Med. Commun.* 31(1):39-45.
[14] Kun-Eek K, et al., (2007) *Nuclear Medicine and Biology*, vol. 34(2), pp: 153-163.
[15] Wang M, et al., (2008) *Applied Radiation and Isotopes*, vol 66(4), pp 506-512.
[16] Mazière m, et al., *Life Sci.* 1981, 7; 29(23):2391-7.
[17] Hansch C, Leo A. Log P Database. Pomona College Medicinal Chemistry Project, Claremont, Calif. 91711. 1987.

SUMMARY OF THE INVENTION

A main prerequisite for a positron emission tomography (PET) tracer to be considered as an optional candidate for myocardial perfusion imaging (MPI) is an elevated myocardial tracer concentration with simultaneous decrease in adjacent compartments, mainly the blood pool and lungs. Rapid and elevated myocardial concentration may be indicative of high tracer extraction during tracer passage through the coronary microcirculation. Rapid washout of tracer from background tissues creates target to non-target image contrast and thus improves the MPI diagnostic process. In addition, a tracer with prolonged stable myocardial activity levels confers an additional advantage, as this quality allows for the performance of the stress test and tracer injection outside the PET room. This is particularly important when a treadmill stress test is clinically indicated or is preferable. Renal excretion of the tracer is also favored over hepatic pathways to minimize the tracer's biological half-life, thus reducing radiation dose to the patient. Labeling the tracer with carbon-11 with its short physical half-life (20.4 min), while restricting its usage to the cyclotron unit's vicinity, is associated, by itself, with favorable radiation dosimetry, and also allows the performance of a rest study an hour and a half after the stress injection without significant residual crosstalk.

The present invention is based on the observed biodistribution in mice and rats and both small- and large-animal imaging using a microPET/CT and a clinical PET/CT, respectively, which supports the superiority of compounds of the invention over those previously known. The results presented herein clearly suggest that organic ammonium salts of the genera disclosed herein offer a great spectrum of advantages and open up the path for new PET applications for MPI. Thus, the invention generally provides novel compounds, compositions comprising same for, e.g., diagnostic applications, pharmaceutical compositions, radiopharmaceuticals and uses thereof in a variety of applications.

In one aspect of the present invention there is provided a radiolabeled compound of Formula (I):

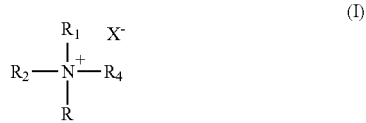

(I)

wherein each of $R_1$, $R_2$, $R_3$ and $R_4$, independently of each other is selected from $C_1$-$C_{10}$ alkyl, $C_2$-$C_{10}$alkenyl, $C_2$-$C_{10}$alkynyl, $C_3$-$C_{10}$cycloalkyl, $C_6$-$C_{18}$aryl, $C_5$-$C_{18}$heteroaryl, $C_1$-$C_{10}$aralkyl, polyethylenglycol (PEG), $C_1$-$C_6$alkyl-O—$CH_2$—$(CH_2$—O—$CH_2)_n$—$CH_2$—OH and $C_1$-$C_6$alkyl-(O—$CH_2$—$CH_2)_m$—OH, each of the aforementioned may optionally be substituted as disclosed herein;

at least one of $R_1$, $R_2$, $R_3$ and $R_4$ is or comprises at least one radiolabeled atom or substituent (which comprises one or more radiolabled atom);

each of n and m, independently of each other is an integer between 2 and 10; and X is a negatively charged pharmaceutically acceptable ion (anion).

Each of the substituents recited above for $R_1$, $R_2$, $R_3$ and $R_4$, independently of each other, is optionally substituted by one or more substituent selected from $C_1$-$C_6$alkyl, $C_6$-$C_{18}$aryl, halide (Cl, Br, I, F), nitro, amine, hydroxyl, ether, and others.

In some embodiments in a compound of Formula (I), each of the alkyl group in said $C_1$-$C_{10}$alkyl, $C_3$-$C_{10}$cycloalkyl, $C_1$-$C_{10}$aralkyl, and polyethyleneglycol (PEG), independently of the other, and irrespective of their position on the ammonium center (namely whether designated as $R_1$, $R_2$, $R_3$ and/or $R_4$) may be substituted as stated above. In some embodiments, the alkyl group is substituted by at least one halide. In other embodiments, the alkyl group is substituted by one or more F atoms.

In some embodiments, where the alkyl group is $C_1$-$C_{10}$alkyl, or $C_1$-$C_{10}$aralkyl, the alkyl group has 1, 2, or 3 carbon atoms, one of which carbon atoms being substituted by one or more F atoms (in some embodiments, 1 carbon atom). In other embodiments, the alkyl group has 1 or 2 carbon atoms, one of which carbon atoms being substituted by one or more F atoms (in some embodiments, 1 carbon atom). For example, where the alkyl group is $C_1$-$C_{10}$alkyl having 2 carbon atoms, the alkyl group is an ethyl group, one of which carbon atoms being substituted by an F atom. Where the alkyl group is polyethylenglycol (PEG), one of the ethylene carbons may be substituted by an F atom.

In some embodiments, at least one of said $R_1$, $R_2$, $R_3$ and $R_4$, independently of the other, is an alkyl group having 1, 2, 3, or 4 carbon atoms, one of which being substituted by one or more F atoms.

In some embodiments, at least one of said $R_1$, $R_2$, $R_3$ and $R_4$, independently of the other, is an alkyl group having 1 or 2 carbon atoms, one of which being substituted by one or more F atoms.

In some embodiments, at least one of said $R_1$, $R_2$, $R_3$ and $R_4$, independently of the other, is an alkyl group having 1 carbon atom (in some embodiments, 2 carbon atoms; in another embodiment 3 carbon atoms), one of which being substituted by one or more F atoms.

In some embodiments, any of the above F atoms substituting an alkyl group is $^{18}$F.

In some embodiments, in a compound of Formula (I), at least one of $R_1$, $R_2$ and $R_3$ is a $C_1$-$C_{10}$alkyl. In other embodiments, at least two of $R_1$, $R_2$ and $R_3$ is a $C_1$-$C_{10}$alkyl. In further embodiments, each of $R_1$, $R_2$ and $R_3$ is a $C_1$-$C_8$alkyl. In each of said embodiments, each of the substituents, independently, is optionally substituted.

In some embodiments, $R_4$ is a radiolabeled $C_1$-$C_8$alkyl.

In other embodiments, at least one of $R_1$, $R_2$ and $R_3$ is a $C_1$-$C_{10}$alkyl and $R_4$ is a $C_6$-$C_{18}$aryl.

In yet additional embodiments, two of $R_1$, $R_2$ and $R_3$ are each, independently, a $C_1$-$C_{10}$alkyl and the other of $R_1$, $R_2$ and $R_3$ is a $C_6$-$C_{18}$aryl and $R_4$ is a $C_6$-$C_{18}$aryl. In such embodiments, for example, each of $R_1$ and $R_2$ is a $C_1$-$C_{10}$alkyl and each of $R_3$ and $R_4$, independently, is a $C_6$-$C_{18}$aryl.

In some embodiments, at least one of $R_1$, $R_2$ and $R_3$ is a $C_6$-$C_{18}$aryl, being optionally substituted. In some embodiments, at least one of $R_1$, $R_2$ and $R_3$ is a $C_6$-$C_{18}$aryl, being optionally substituted, and $R_4$ is a $C_1$-$C_{10}$alkyl.

In some embodiments, each of $R_1$, $R_2$, $R_3$ and $R_4$, independently of each other, is an optionally substituted $C_1$-$C_{10}$alkyl.

In some embodiments, at least one of said $R_1$, $R_2$, $R_3$ and $R_4$ is a $C_1$-$C_{10}$alkyl different from a methyl, and at least one of said $R_1$, $R_2$, $R_3$ and $R_4$ is a methyl group. The $C_1$-$C_{10}$alkyl may or may not be substituted.

In some embodiments, each of $R_1$, $R_2$, $R_3$ and $R_4$ is a methyl group, at least one which being radiolabeled. An exemplary compound is Compound [$^{11}$C]-1.

In some embodiments, two of $R_1$, $R_2$, $R_3$ and $R_4$, independently of each other, is an optionally substituted $C_1$-$C_{10}$alkyl and the other two of $R_1$, $R_2$, $R_3$ and $R_4$, independently of the other, is an optionally substituted $C_6$-$C_{18}$aryl.

In some embodiments, three of $R_1$, $R_2$, $R_3$ and $R_4$, independently of each other, is an optionally substituted $C_1$-$C_6$alkyl and the other one of $R_1$, $R_2$, $R_3$ and $R_4$ is an optionally substituted $C_6$-$C_{18}$aryl.

In other embodiments, in a compound according to Formula (I), $R_1$ is a $C_6$-$C_{18}$aryl, said aryl being in certain embodiments a substituted or unsubstituted phenyl ring. Thus, the compound is of Formula (II):

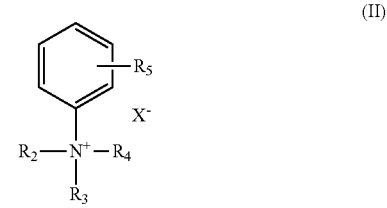

(II)

wherein each of $R_2$, $R_3$ and $R_4$, independently of each other is selected from $C_1$-$C_{10}$ alkyl, $C_2$-$C_{10}$alkenyl, $C_2$-$C_{10}$alkynyl, $C_3$-$C_{10}$cycloalkyl, $C_6$-$C_{18}$aryl, $C_5$-$C_{18}$heteroaryl, $C_1$-$C_{10}$aralkyl, polyethylenglycol (PEG), $C_1$-$C_6$alkyl-O—$CH_2$—$(CH_2$—O—$CH_2)_n$—$CH_2$—OH and $C_1$-$C_6$alkyl-(O—$CH_2$—$CH_2)_m$, —OH;

at least one of $R_2$, $R_3$ and $R_4$ is or comprises at least radiolabeled atom or substituent;

$R_5$ is one or two (referred to as $R_5^1$, $R_5^2$) or three (referred to as $R_5^1$, $R_5^2$, $R_5^3$) or four (referred to as $R_5^1$, $R_5^2$, $R_5^3$, $R_5^4$) or five substitutions (referred to as $R_5^1$, $R_5^2$, $R_5^3$, $R_5^4$, $R_5^5$) on the ring, the substituting group being selected from —H, halide (i.e., Cl, Br, I, F), nitro (—NO$_2$), amine (—NH$_2$, —NH—$C_1$-$C_6$alkyl, —N($C_1$-$C_6$alkyl)$_2$), hydroxyl (—OH), $C_1$-$C_6$alkyl, $C_2$-$C_6$alkenyl, $C_2$-$C_6$alkynyl, $C_3$-$C_6$cycloalkyl, $C_1$-$C_6$alkoxy (—O—$C_1$-$C_6$alkyl), $C_6$-$C_{18}$aryl, $C_5$-$C_{10}$heteroaryl, $C_1$-$C_{10}$aralkyl, polyethylenglycol (PEG), $C_1$-$C_6$alkyl-O—CH$_2$—(CH$_2$—O—CH$_2$)$_z$—CH$_2$—OH and $C_1$-$C_6$alkyl-(O—CH$_2$—CH$_2$)$_y$—OH;

each of n and m, independently of each other is an integer between 2 and 10;

each of z and y, independently of each other is an integer between 2 and 10; and X is a negatively charged pharmaceutically acceptable ion (anion).

In some embodiments, in a compound of Formula (II), at least one of $R_2$, $R_3$, and $R_4$, independently of the other, is a $C_1$-$C_{10}$alkyl. In some further embodiments, one of $R_2$, $R_3$, and $R_4$ is a $C_1$-$C_{10}$ alkyl, and another of $R_2$, $R_3$, and $R_4$ is PEG. In further embodiments, two of said at least one of $R_2$, $R_3$, and $R_4$ is a $C_1$-$C_{10}$ alkyl and the third of said one of $R_2$, $R_3$, and $R_4$ is PEG.

In some embodiments, in a compound of Formula (II), at least one of $R_2$, $R_3$, and $R_4$, independently of the other, is a $C_1$-$C_{10}$alkyl, one of which being substituted with one or more F atoms (1, 2, or 3 F atoms; in some embodiments-1 F atom). In some further embodiments, one of $R_2$, $R_3$, and $R_4$ is a $C_1$-$C_{10}$alkyl, and another of $R_2$, $R_3$, and $R_4$ is PEG, one or both of $C_1$-$C_{10}$alkyl and PEG is substituted with one or more F atoms (1, 2, or 3 F atoms; in some embodiments-1 F atom). In further embodiments, two of said at least one of $R_2$, $R_3$, and $R_4$ is a $C_1$-$C_{10}$alkyl and the third of said one of $R_2$, $R_3$, and $R_4$ is PEG, wherein one or both of said $C_1$-$C_{10}$alkyl and/or said PEG is substituted with one or more F atoms (1, 2, or 3 F atoms; in some embodiments-1 F atom).

In some embodiments, in a compound of Formula (II), each of $R_2$, $R_3$ and $R_4$ is a $C_1$-$C_{10}$alkyl, at least one of said $R_2$, $R_3$ and $R_4$ comprising at least one radiolabeled atom or substituent.

In other embodiments, in a compound of Formula (II), at least one of $R_5^1$, $R_5^2$, $R_5^3$, $R_5^4$, $R_5^5$ is —H or a $C_1$-$C_{10}$alkyl.

In further embodiments, each of $R_5^1$, $R_5^2 R_5^3 R_5^4 R_5^5$ is —H, $R_2$, each of $R_2$, $R_3$ and $R_4$, independently of the other is a radiolabeled $C_1$-$C_{10}$alkyl selected from a methyl, ethyl, propyl, iso-propyl and n-butyl.

In other embodiments, each of $R_2$, $R_3$ and $R_4$, independently of the other is a radiolabeled methyl or an ethyl.

In further embodiments, each of $R_2$, $R_3$ and $R_4$ is a methyl, one of said methyl groups being radiolabeled. An exemplary compound is thus Compound [$^{11}$C]-2 of the invention.

In other embodiments, $R_5$ is one or more substituents, as detailed hereinabove, each being independently selected from halide (i.e., Cl, Br, I, F), nitro (—NO$_2$), amine (—NH$_2$, —NH—$C_1$-$C_{10}$alkyl, —N($C_1$-$C_{10}$alkyl)$_2$), hydroxyl (—OH), $C_1$-$C_{10}$alkyl, $C_2$-$C_6$alkenyl, $C_2$-$C_6$alkynyl, $C_3$-$C_6$cycloalkyl, $C_1$-$C_{10}$alkoxy (—O—$C_1$-$C_{10}$alkyl), $C_6$-$C_{18}$aryl, $C_5$-$C_{10}$heteroaryl, $C_1$-$C_{10}$aralkyl, polyethylenglycol (PEG), $C_1$-$C_6$alkyl-O—CH$_2$—(CH$_2$—O—CH$_2$)$_z$—CH$_2$—OH and $C_1$-$C_6$alkyl-(O—CH$_2$—CH$_2$)$_y$—OH.

In some embodiments, $R_5$ is a single substituent at ay position of the phenyl ring (substituting any of the 5 ring hydrogens). In some embodiments, $R_5$ is a single substituent at the ortho position. In some embodiments, $R_5$ is a single substituent at the meta position. In some embodiments, $R_5$ is a single substituent at the para position.

In further embodiments, $R_5$ is a halide (i.e., Cl, Br, I, F), an amine (—NH$_2$, —NH—$C_1$-$C_{10}$alkyl, —N($C_1$-$C_{10}$alkyl)$_2$), an hydroxyl (—OH), or a $C_1$-$C_{10}$alkyl. In some embodiments, $R_5$ is —NH$_2$. In further embodiments, $R_5$ is —N($C_1$-$C_{10}$alkyl)$_2$, wherein each of the two $C_1$-$C_{10}$alkyl groups in —N($C_1$-$C_6$alkyl)$_2$ is same or different. In some embodiments, the two $C_1$-$C_{10}$alkyl groups in —N($C_1$-$C_{10}$alkyl)$_2$ are the same, being selected from methyl and ethyl. In further embodiments, each of the two groups is a methyl. A non-limiting example of such a compound is Compound [$^{11}$C]-3.

In other embodiments, $R_5$ is a $C_1$-$C_{10}$alkyl. In some embodiments, is the $C_1$-$C_{10}$alkyl is selected from a methyl, ethyl, propyl, iso-propyl and n-butyl. In some embodiments, the $C_1$-$C_{10}$alkyl is a methyl group. A non-limiting example is Compound [$^{11}$C]-6.

In still other embodiments, in a compound according to Formula (I), $R_1$ is a $C_6$-$C_{18}$aryl, said aryl being different from a phenyl. In some embodiments, the $C_6$-$C_{18}$aryl is a naphthyl and the compound is of Formula (III):

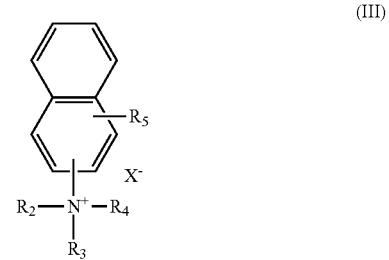

(III)

wherein the naphthyl moiety may be bonded to the N atom of the quarternary ammonium group via any of the naphthyl carbon atoms, and wherein each of $R_2$, $R_3$ and $R_4$, independently of each other is selected from $C_1$-$C_{10}$ alkyl, $C_2$-$C_{10}$alkenyl, $C_2$-$C_{10}$alkynyl, $C_3$-$C_{10}$cycloalkyl, $C_6$-$C_{18}$aryl, $C_5$-$C_{18}$heteroaryl, $C_1$-$C_{10}$aralkyl, polyethylenglycol (PEG), $C_1$-$C_6$alkyl-O—CH$_2$—(CH$_2$—O—CH$_2$)$_n$—CH$_2$—OH and $C_1$-$C_6$alkyl-(O—CH$_2$—CH$_2$)$_m$—OH;

at least one of $R_2$, $R_3$ and $R_4$ is or comprises at least radiolabeled atom or substituent;

$R_5$ is one or two or three or four or five or six or seven substitutions on the naphthyl ring, the substituting group being selected from —H, halide (i.e., Cl, Br, I, F), nitro (—NO$_2$), amine (—NH$_2$, —NH—$C_1$-$C_{10}$alkyl, —N($C_1$-$C_{10}$alkyl)$_2$), hydroxyl (—OH), $C_1$-$C_{10}$alkyl, $C_2$-$C_6$alkenyl, $C_2$-$C_6$alkynyl, $C_3$-$C_6$cycloalkyl, $C_1$-$C_{10}$alkoxy (—O—$C_1$-$C_{10}$alkyl), $C_6$-$C_{10}$aryl, $C_5$-$C_{10}$heteroaryl, $C_1$-$C_{10}$aralkyl, polyethylenglycol (PEG), $C_1$-$C_6$alkyl-O—CH$_2$—(CH$_2$—O—CH$_2$)$_z$—CH$_2$—OH and $C_1$-$C_6$alkyl-(O—CH$_2$—CH$_2$)$_y$—OH;

each of n and m, independently of each other is an integer between 2 and 10;

each of z and y, independently of each other is an integer between 2 and 10; and X is a negatively charged pharmaceutically acceptable ion (anion).

In some embodiments, in a compound of Formula (III), at least one of $R_2$, $R_3$, and $R_4$, independently of the other, is a $C_1$-$C_{10}$alkyl. In some further embodiments, one of $R_2$, $R_3$, and $R_4$ is a $C_1$-$C_{10}$ alkyl, and another of $R_2$, $R_3$, and $R_4$ is PEG. In further embodiments, two of said at least one of $R_2$, $R_3$, and $R_4$ is a $C_1$-$C_{10}$ alkyl and the third of said one of $R_2$, $R_3$, and $R_4$ is PEG.

In some embodiments, in a compound of Formula (III), at least one of $R_2$, $R_3$, and $R_4$, independently of the other, is a $C_1$-$C_{10}$alkyl, one of which being substituted with one or more F atoms (1, 2, or 3 F atoms; in some embodiments-1 F atom). In some further embodiments, one of $R_2$, $R_3$, and $R_4$ is a $C_1$-$C_{10}$alkyl, and another of $R_2$, $R_3$, and $R_4$ is PEG, one or both of $C_1$-$C_{10}$alkyl and PEG is substituted with one or more F atoms (1, 2, or 3 F atoms; in some embodiments-1 F atom). In further embodiments, two of said at least one of $R_2$, $R_3$, and $R_4$ is a $C_1$-$C_{10}$alkyl and the third of said one of $R_2$, $R_3$, and $R_4$ is PEG, wherein one or both of said $C_1$-$C_{10}$alkyl and/or said PEG is substituted with one or more F atoms (1, 2, or 3 F atoms; in some embodiments-1 F atom).

In some embodiments, the compound of Formula (III) is of the Formula (IV):

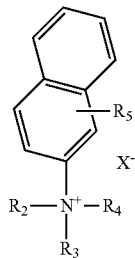

(IV)

wherein each of $R_2$, $R_3$, $R_4$ and $R_5$ is as defined above.

In some embodiments, $R_5$ is —H.

In some embodiments, in a compound of Formula (IV), at least one of $R_2$, $R_3$, and $R_4$, independently of the other, is a $C_1$-$C_{10}$alkyl. In some further embodiments, one of $R_2$, $R_3$, and $R_4$ is a $C_1$-$C_{10}$ alkyl, and another of $R_2$, $R_3$, and $R_4$ is PEG. In further embodiments, two of said at least one of $R_2$, $R_3$, and $R_4$ is a $C_1$-$C_{10}$ alkyl and the third of said one of $R_2$, $R_3$, and $R_4$ is PEG.

In some embodiments, in a compound of Formula (IV), at least one of $R_2$, $R_3$, and $R_4$, independently of the other, is a $C_1$-$C_{10}$alkyl, one of which being substituted with one or more F atoms (1, 2, or 3 F atoms; in some embodiments-1 F atom). In some further embodiments, one of $R_2$, $R_3$, and $R_4$ is a $C_1$-$C_{10}$alkyl, and another of $R_2$, $R_3$, and $R_4$ is PEG, one or both of $C_1$-$C_{10}$alkyl and PEG is substituted with one or more F atoms (1, 2, or 3 F atoms; in some embodiments-1 F atom). In further embodiments, two of said at least one of $R_2$, $R_3$, and $R_4$ is a $C_1$-$C_{10}$alkyl and the third of said one of $R_2$, $R_3$, and $R_4$ is PEG, wherein one or both of said $C_1$-$C_{10}$alkyl and/or said PEG is substituted with one or more F atoms (1, 2, or 3 F atoms; in some embodiments-1 F atom).

In further embodiments, in a compound of Formula (IV), each of $R_2$, $R_3$ and $R_4$ is a $C_1$-$C_{10}$alkyl, at least one of said $R_2$, $R_3$ and $R_4$ comprising at least one radiolabeled atom or substituent.

In further embodiments, each of $R_2$, $R_3$ and $R_4$, independently of the other is a radiolabeled $C_1$-$C_{10}$alkyl selected from a methyl, ethyl, propyl, iso-propyl and n-butyl.

In other embodiments, each of $R_2$, $R_3$ and $R_4$, independently of the other is a radiolabeled methyl or an ethyl.

In further embodiments, each of $R_2$, $R_3$ and $R_4$ is a methyl, one of said methyl groups being radiolabeled. An exemplary compound is thus Compound [$^{11}$C]-7 of the invention.

In other embodiments, in a compound according to Formula (I), each of $R_1$ and $R_2$ is a $C_6$-$C_{18}$aryl, said aryl being in certain embodiments a substituted or unsubstituted phenyl ring. Thus, the compound is of Formula (V):

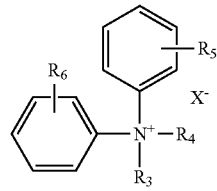

(V)

wherein each of $R_3$ and $R_4$, independently of the other is selected from $C_1$-$C_{10}$ alkyl, $C_2$-$C_{10}$alkenyl, $C_2$-$C_{10}$alkynyl, $C_3$-$C_{10}$cycloalkyl, $C_6$-$C_{18}$aryl, $C_5$-$C_{18}$heteroaryl, $C_1$-$C_{10}$aralkyl, polyethylenglycol (PEG), $C_1$-$C_6$alkyl-O—CH$_2$—(CH$_2$—O—CH$_2$)$_n$—CH$_2$—OH and $C_1$-$C_6$alkyl-(O—CH$_2$—CH$_2$)$_m$—OH;

at least one of $R_3$ and $R_4$ is or comprises at least radiolabeled atom or substituent;

each of $R_5$ and $R_6$, independently of the other, is one or two or three or four or five substitutions on the respective rings (as detailed hereinabove), the substituting group being selected from —H, halide (i.e., Cl, Br, I, F), nitro (—NO$_2$), amine (—NH$_2$, —NH—C$_1$-C$_{10}$alkyl, —N(C$_1$-C$_{10}$alkyl)$_2$), hydroxyl (—OH), $C_1$-$C_{10}$alkyl, $C_2$-$C_6$alkenyl, $C_2$-$C_6$alkynyl, $C_3$-$C_6$cycloalkyl, $C_1$-$C_{10}$alkoxy (—O—$C_1$-$C_{10}$alkyl), $C_6$-$C_{18}$aryl, $C_5$-$C_{10}$heteroaryl, $C_1$-$C_{10}$aralkyl, polyethylenglycol (PEG), $C_1$-$C_6$alkyl-O—CH$_2$—(CH$_2$—O—CH$_2$)$_z$—CH$_2$—OH and $C_1$-$C_6$alkyl-(O—CH$_2$—CH$_2$)$_y$—OH;

each of n and m, independently of each other is an integer between 2 and 10;

each of z and y, independently of each other is an integer between 2 and 10; and X is a negatively charged pharmaceutically acceptable ion (anion).

As used herein, "an integer between 2 and 10" is 2, 3, 4, 5, 6, 7, 8, 9, or 10. Any of the aforementioned integers may constitute n, m, z or y independently.

In some embodiments, in a compound of Formula (V), each of $R_3$ and $R_4$ is a $C_1$-$C_{10}$alkyl, at least one of said $R_3$ and $R_4$ comprising at least one radiolabeled atom or substituent.

In other embodiments, in a compound of Formula (V), at least one of the substituting $R_5$, and/or $R_6$, representing a single substituting or multiple substituting groups is —H or a $C_1$-$C_{10}$alkyl.

In some embodiments, in a compound of Formula (V), at least one of $R_3$, and $R_4$, independently of the other, is a $C_1$-$C_{10}$alkyl. In some further embodiments, one of $R_3$, and $R_4$ is a $C_1$-$C_{10}$ alkyl, and the other of $R_3$, and $R_4$ is PEG. In further embodiments, each $R_3$ and $R_4$ is a $C_1$-$C_{10}$ alkyl.

In some embodiments, in a compound of Formula (V), at least one of $R_3$, and $R_4$, independently of the other, is a $C_1$-$C_{10}$alkyl, one of which being substituted with one or more F atoms (1, 2, or 3 F atoms; in some embodiments-1 F atom). In some further embodiments, one of $R_3$ and $R_4$ is a $C_1$-$C_{10}$alkyl, and the other of $R_3$ and $R_4$ is PEG, one or both of $C_1$-$C_{10}$alkyl and PEG is substituted with one or more F atoms (1, 2, or 3 F atoms; in some embodiments-1 F atom). In further embodiments, both $R_3$ and $R_4$ is a $C_1$-$C_{10}$alkyl, wherein one or both of said $C_1$-$C_{10}$alkyl is substituted with one or more F atoms (1, 2, or 3 F atoms; in some embodiments-1 F atom).

In further embodiments, each of $R_5$ and/or $R_6$ is —H, each of $R_3$ and $R_4$, independently of the other is a radiolabeled $C_1$-$C_{10}$ alkyl selected from a methyl, ethyl, propyl, iso-propyl and n-butyl.

In other embodiments, each of $R_3$ and $R_4$, independently of the other is a radiolabeled methyl or ethyl.

In further embodiments, each of $R_3$ and $R_4$ is methyl, one of said methyl groups being radiolabeled. An exemplary compound is thus Compound [$^{11}$C]-4 of the invention.

In other embodiments, at least one of $R_3$ and $R_4$ is not a methyl group. In some embodiments, at least one of $R_3$ and $R_4$ is an ethyl group and the other of $R_3$ and $R_4$ is a methyl group. One of said of $R_3$ and $R_4$ is optionally substituted. An exemplary compound is Compound [$^{18}$]-5.

As used herein, the term "—$(C_1$-$C_{10})$alkyl" refers to a straight or branched aliphatic chain containing between 1 and 10 carbon atoms, which may or may not be substituted. In some embodiments, the —$(C_1$-$C_{10})$alkyl is an alkyl group having 1, 2, 3, 4, 5, 6, 7, 8, 9 or 10 carbon atoms. In some embodiments, said —$(C_1$-$C_{10})$alkyl is an alkyl group having 1, 2, 3, 4, or 5 carbon atoms. In other embodiments, said —$(C_1$-$C_{10})$alkyl is an alkyl having 1, 2, or 3 carbon atoms. In further embodiments, said —$(C_1$-$C_{10})$alkyl is an alkyl having 1 or 2 carbon atoms.

Thus, the term "—$(C_1$-$C_{10})$alkyl" encompasses the various ranges of carbon atom numbers. The term encompasses and is interchangeable with $C_1$-$C_2$ alkyl, $C_2$-$C_3$alkyl, $C_3$-$C_4$alkyl, $C_4$-$C_5$alkyl, $C_5$-$C_6$alkyl, $C_6$-$C_7$alkyl, $C_7$-$C_8$alkyl, $C_8$-$C_9$alkyl, $C_9$-$C_{10}$ alkyl, $C_1$-$C_3$alkyl, $C_2$-$C_4$alkyl, $C_3$-$C_5$alkyl, $C_4$-$C_6$alkyl, $C_5$-$C_7$alkyl, $C_6$-$C_8$alkyl, $C_7$-$C_9$alkyl, $C_8$-$C_{10}$alkyl, $C_1$-$C_4$alkyl, $C_2$-$C_5$alkyl, $C_3$-$C_6$alkyl, $C_4$-$C_7$alkyl, $C_5$-$C_8$alkyl, $C_6$-$C_9$alkyl, $C_7$-$C_{10}$alkyl, $C_1$-$C_5$alkyl, $C_2$-$C_6$alkyl, $C_3$-$C_7$alkyl, $C_4$-$C_8$alkyl, $C_5$-$C_9$alkyl, $C_6$-$C_{10}$alkyl, $C_1$-$C_6$alkyl, $C_2$-$C_7$alkyl, $C_3$-$C_8$alkyl, $C_4$-$C_9$alkyl, $C_5$-$C_{10}$alkyl, $C_1$-$C_7$alkyl, $C_2$-$C_8$alkyl, $C_3$-$C_9$alkyl, $C_4$-$C_{10}$alkyl, $C_1$-$C_8$alkyl, $C_2$-$C_9$alkyl, $C_3$-$C_{10}$alkyl, $C_1$-$C_9$alkyl, $C_2$-$C_{10}$alkyl, $C_1$alkyl, $C_2$alkyl, $C_3$alkyl, $C_4$alkyl, $C_5$alkyl, $C_6$alkyl, $C_7$alkyl, $C_8$alkyl, $C_9$alkyl or $C_{10}$alkyl.

In some embodiments, wherein, for example, $R_1$ and $R_2$ (or any other groups or group combination) are said to independently of each other be selected from $C_1$-$C_{10}$alkyl, the alkyl groups need not be the same, in terms of length, nor in terms of substitution. For example, in some cases $R_1$ may be a $C_1$-$C_{10}$alkyl selected amongst $C_1$-$C_3$alkyls and $R_2$ may a $C_1$-$C_{10}$alkyl selected amongst $C_3$-$C_7$alkyls.

Non-limiting examples of such alkyl chains include methyl, ethyl, propyl, iso-propyl, iso-butyl, n-butyl, sec-butyl, tert-butyl, pentyl, iso-hexyl, heptyl, octyl, nonyl and decyl.

In some embodiments, the —$(C_1$-$C_{10})$alkyl is a methyl.

In other embodiments, the —$(C_1$-$C_{10})$alkyl is different from a methyl (namely, may be an alkyl having 2, or 3, or 4, or 5, or 6, or 7, or 8, or 9, or 10 carbon atoms).

Where reference is made to "—$(C_1$-$C_6)$alkyl" the —$(C_1$-$C_6)$alkyl is an alkyl group having 1, 2, 3, 4, 5 or 6 carbon atoms. In some embodiments, said —$(C_1$-$C_6)$alkyl is an alkyl group having 1, 2, 3, 4, or 5 carbon atoms. In other embodiments, said —$(C_1$-$C_6)$alkyl is an alkyl having 1, 2, or 3 carbon atoms. In further embodiments, said —$(C_1$-$C_6)$alkyl is an alkyl having 1 or 2 carbon atoms.

Thus, the term "—$(C_1$-$C_6)$alkyl" encompasses the various ranges of carbon atom numbers. The term encompasses and is interchangeable with $C_1$-$C_2$ alkyl, $C_2$-$C_3$alkyl, $C_3$-$C_4$alkyl, $C_4$-$C_5$alkyl, $C_5$-$C_6$alkyl, $C_1$-$C_3$alkyl, $C_2$-$C_4$alkyl, $C_3$-$C_5$alkyl, $C_4$-$C_6$alkyl, $C_1$-$C_4$alkyl, $C_2$-$C_1$alkyl, $C_3$-$C_1$alkyl, $C_1$-$C_1$alkyl, $C_2$-$C_1$alkyl, $C_1$alkyl, $C_1$alkyl, $C_1$alkyl, $C_4$alkyl, $C_1$alkyl, or $C_1$alkyl.

In some embodiments, any of the alkyl groups disclosed herein in reference to a compound of Formula (I), (II), (III), (IV) or (V) may be substituted with one or more F atoms, as recited hereinabove with reference to a compound of Formula (I).

As used herein, the term "—$N((C_1$-$C_{10})$alkyl)$_2$" refers to a secondary amine (wherein one of $R_7$ and $R_8$ is a $(C_1$-$C_{10})$ alkyl), wherein the two —$(C_1$-$C_{10})$alkyl groups may be the same or different. The —$(C_1$-$C_{10})$alkyl is as defined above. The N atom may be further protonated or alkylated to a charged state, forming a salt with, e.g., at least one pharmaceutically acceptable counterion.

In some embodiments, in the —$N((C_1$-$C_{10})$alkyl)$_2$ group, the two —$(C_1$-$C_{10})$alkyl groups form a cyclic structure with the N atom they are bonded to; the cyclic amine having between 3 and 6 atoms in the heteroring structure. In some embodiments, the heteroring comprises, apart from the N atom, one or more additional heteroatoms selected from N, O and S. In further embodiments, the heteroring comprises a single heteroatom (the N atom of the —$N((C_1$-$C_{10})$alkyl)$_2$) with the remaining atoms being carbon atoms.

As used herein, "—$(C_6$-$C_{18})$aryl" refers, in the context of the present invention, to an aromatic ring system having between 6 and 18 carbon atoms. In some embodiments, the aryl is a substituted or unsubstituted phenyl or a substituted or unsubstituted naphthyl group.

As known in the art, polyethylenglycol (PEG) is an ether of the general formula —$(O$—$CH_2$—$CH_2)_k$—$OH$. In accordance with the present invention, the PEG moiety may be associated with the N atom of the ammonium molecule via the bond N—O, wherein N is the ammonium N atom and O is the PEG end-chain atom, or via a carbon spacer (linker) such as an alkyl. In some embodiments, the PEG is associated directly with the N atom of the ammonium molecule. In other embodiments, the PEG is associated through a carbon spacer affording, e.g., $C_1$-$C_6$alkyl-$(O$—$CH_2$—$CH_2)_y$—$OH$, wherein y is as defined above. In the general formula —$(O$—$CH_2$—$CH_2)_k$—$OH$ representing PEG, k is an integer between 2 and 10. K may be 2, 3, 4, 5, 6, 7, 8, 9, or 10.

In reference to groups $R_5$ and $R_6$, substituting on an aryl moiety, it is said that each represents "one or two or three or four or five substitutions on the ring". In this context, it should be noted that one ring may be substituted by a single substituent ($R_5$) and the other ring may be substituted by more than one substituent ($R_6$), as selected above. When the ring bearing the group $R_5$ and/or the ring bearing the group $R_6$ is substituted by a single substituting group, the single group may be substituted on any one of the ring positions, i.e., ortho, meta, or para. When the ring(s) is substituted by two substituting groups, the two groups may be on neighboring carbon atoms (ortho to each other), or may be separated by one or more carbon atoms. When the ring(s) is substituted by three or more substituting groups, the groups may be substituted on any one of the ring positions at any variation available.

The negatively charged "pharmaceutically acceptable ion" (anion), being X in the general formula (I) is an anion derived from an inorganic acid or from an organic acid. In some embodiments, the pharmaceutically acceptable anion is derived from inorganic acids thus may be selected from sulfate, pyrosulfate, bisulfate, sulfite, bisulfite, nitrate, phosphate, monohydrogenphosphate, dihydrogenphosphate, metaphosphate, pyrophosphate, chloride, bromide, iodide, acetate, propionate, caprylate, isobutyrate, oxalate, malonate, succinate, suberate, sebacate, fumarate, maleate, mandelate, benzoate, chlorobenzoate, methylbenzoate, dinitrobenzoate, phthalate, benzenesulfonate, toluenesulfonate, phenylacetate, citrate, lactate, maleate, tartrate, methanesulfonate, and the like. Also contemplated are salts of amino acids such as arginate and the like and gluconate, galacruronate (For further anions suitable in compounds of the invention, see, for example, Berge S. M., et al., "Pharmaceutical Salts," J. of Pharmaceutical Science, 66:1-19 (1977)).

The invention also provides a compound selected from:
Compound 1: [$^{11}$C]tetramethyl-ammonium iodide (herein designated [$^{11}$C]-1),
Compound 2: [$^{11}$C]trimethyl-phenyl-ammonium iodide (herein designated [$^{11}$C]-2),
Compound 3: [$^{11}$C](4-dimethylamino-phenyl)-trimethyl-ammonium iodide (herein designated [$^{11}$C]-3),
Compound 4: [$^{11}$C]dimethyl-diphenyl-ammonium iodide (herein designated [$^{11}$C]-4),
Compound 5: 2-[$^{18}$F]fluoro-ethyl)-methyl-diphenyl-ammonium trifluoro-methanesulfonate (herein designated [$^{18}$F]-5),
Compound 6: [$^{11}$C]Methyl-dimethyl-m-tolyl-ammonium iodide (herein designated [$^{11}$C]-6),
Compound 7: [$^{11}$C]Methyl-dimethyl-1-naphtylammonium trifluoro-methane-sulfonate (herein designated [$^{11}$C]-7).

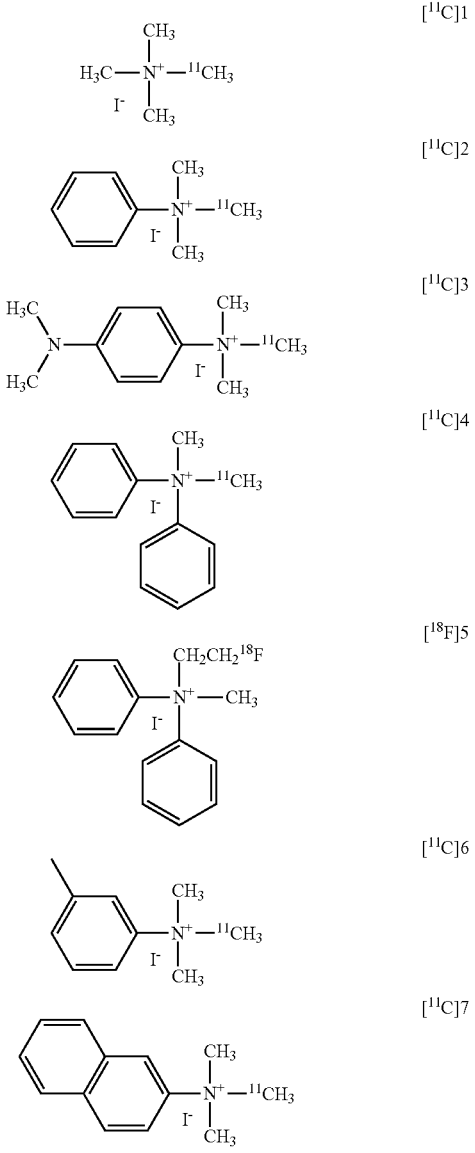

In a further aspect of the present invention there is provided a radiopharmaceutical being or comprising a compound of Formula (I) or any of Formula (II), (III), (IV) and (V), as defined herein.

As used herein, the term "radiopharmaceutical" (or 'radiopharmaceutical formulation') refers to a formulation comprising at least one compound of general Formulae disclosed herein, as defined herein, namely at least one radiolabeled tracer, in a form suitable for administration to a mammal, such as a human. The tracer may be radiolabeled by any radioisotope known. In some embodiments, the radioisotope used for labeling the tracer is selected from $^{18}$F, $^{15}$O, $^{13}$N and $^{11}$C.

In some embodiments, the radioisotope is $^{11}$C.
In some embodiments, the radioisotope is $^{18}$F.
In some embodiments, the radioisotope is $^{13}$N.
In some embodiments, the radioisotope is not $^{18}$F.

Typically, the radioisotope is $^{11}$C or a radioisotope bonded directly to at least one of the alkyl groups in the formulae of the invention. The radioisotope is typically not bonded to an aryl (e.g., phenyl, naphthyl) group.

In some embodiments, where the radioisotope is $^{18}$F it is not bonded to an aryl (e.g., phenyl, naphthyl) group but rather to an alkyl group.

The radiopharmaceutical may be in the form of an aqueous solution. The radiopharmaceutical formulation may optionally further comprise additional components such as a pH-adjusting agent, pharmaceutically acceptable stabilizers or antioxidants (such as ascorbic acid, gentisic acid or para-aminobenzoic acid), an antimicrobial preservative, an organic solvent (such as ethanol) or filler. The radiopharmaceutical, as defined herein, is typically administered in an amount to provide a dependable image considering the nature of the disease or condition being detected, the patient's weight, size, Waist-Hip Ratio (WHR), Body Surface Area (BSA), Body Mass Index (BMI) and such other factors as would be apparent to a person skilled in the art.

As a general rule to be applied for the radiopharmaceutical, as defined herein, the aim is to have the lowest quantities of excipients possible that produce a pharmaceutically effective as well as physiologically tolerable radiopharmaceutical formulation.

The radiopharmaceutical, as defined herein, contains, inter alia, a suitable amount of the radiolabeled compound of the general Formula (I). For use in positron emission tomography (PET) the amount is between about 5 to between about 20 mCi, preferably 10 to 15 mCi. For use in single photon emission computed tomography (SPECT) the amount is between about 0.1 to between about 30 mCi, preferably 10 to 20 mCi.

In some embodiments, the radiopharmaceutical, as defined herein, is for use in the diagnosis of a disease or disorder.

In other embodiments, the radiopharmaceutical, as defined herein, is for use in risk stratification.

In some embodiments, the disease or disorder is selected from a cardiac disease, renal, neuronal and neoplastic diseases or disorders.

As used herein, the term "cardiac disease" refers to any disease that involves the heart or blood vessels (e.g. coronary artery disease) including diseases related to atherosclerosis (arterial disease). In some embodiments, the disease or disorder is a coronary artery disease.

As used herein, the term "coronary artery disease" refers to any disease or disorder which involves the complete or partial blockage of the blood vessels that supply blood and oxygen to the heart and/or which may involve the symptoms of chest heaviness, dyspnea, fatigue, chest pain, angina or myocardial infarction. Coronary artery disease according to the present invention refers to the entire spectrum of coronary artery diseases.

The present invention also provides the use of at least one compound of Formula (I), as defined herein, for the preparation of a radiopharmaceutical.

In a further of its aspects, the present invention provides the use of at least one compound of Formula I, as defined herein, or of at least one radiopharmaceutical, as defined herein, in the preparation of a composition.

In some embodiments, the composition is a diagnostic composition.

As defined herein the term "diagnostic composition" refers to a composition which is suitable for use as a biomarker for diagnosis of various disease and disorders in human and non-human subjects using molecular imaging. In some embodiments, the molecular imaging is a non-invasive molecular imaging technique selected from myocardial perfusion imaging (MPI), Positron Emission Tomography (PET) or Single Photon Emission Computed Tomography (SPECT) and other methods of non-invasive molecular imaging techniques known to a person skilled in the art.

In some embodiments, the molecular imaging technique is PET.

In some embodiments, the diagnostic composition is for use in the diagnosis of a disease or disorder, as defined herein.

In some embodiments, an additional noninvasive imaging modality (e.g. stress echocardiography) is used sequentially or concurrently with the methods of MPS, PET or SPECT in which the diagnostic composition, compound of Formula (I) or radiopharmaceutical, as defined herein, are used.

The diagnostic composition, as defined herein, may be used for human or animal purposes. The term "animal" refers to a non-human animal.

The diagnostic composition may comprise at least one compound of the Formula (I), as defined herein, and/or at least one radiopharmaceutical, as defined herein, and at least one further pharmaceutically acceptable carrier, diluent, excipient, preservative, solubilizer, emulsifier, and/or adjuvant. The diagnostic composition may be a liquid or lyophilized or otherwise dried formulation and include diluents of various buffer content (e.g.; Tris-HCL, acetate, phosphate), pH and ionic strength, additives such as albumin or gelatin to prevent absorption to surfaces, detergents (e.g., Tween 20, Tween 80, Pluronic F68, bile acid salts), organic solvents (e.g. ethanol), solubilizing agents (e.g., glycerol, polyethylene glycerol), anti-oxidants (e.g., ascorbic acid, sodium metabisulfite), preservatives (e.g., Thimerosal, benzyl alcohol, parabens), bulking substances or tonicity modifiers (e.g., lactose, mannitol), covalent attachment of polymers such as polyethylene glycol to the protein, complexation with metal ions, or incorporation of the material into or onto particulate preparations of polymeric compounds such as polylactic acid, polglycolic acid, hydrogels, etc, or onto liposomes, microemulsions, micelles, unilamellar or multilamellar vesicles, erythrocyte ghosts, or spheroplasts. Such compositions will influence the physical state, solubility, stability, rate of in vivo release, and rate of in vivo clearance. Controlled or sustained release compositions include formulation in lipophilic depots (e.g., fatty acids, waxes, oils).

The diagnostic composition may typically comprise at least one radiolabeled compound according to the invention, namely at least one $^{11}C$, $^{18}F$, $^{15}O$ or $^{13}N$ radiolabeled tracer. The selection of the appropriate tracer as a biomarker for diagnosis, particularly one which employs PET, and to some extent the amount of the biomarker, depends on a variety of factors which are known to a person skilled in the art. In some embodiments, the diagnostic composition comprises a single biomarker (tracer). In other embodiments, the diagnostic composition comprises at least two such biomarkers, one of which may or may not be a biomarker according to the invention.

In some other embodiments, the diagnostic composition, as defined herein is used alongside tracers radiolabeled with a different tracer than the one used in the diagnostic composition of the invention.

In some embodiments, the diagnostic composition is used in the diagnosis of a cardiac disease, as defined herein.

In some embodiments, the diagnostic composition is used in the prognosis and risk stratification of cardiac disease in patients with known or suspected cardiac disease.

In other embodiments, the diagnostic composition is used in the prediction of functional recovery following acute myocardial infarction.

In yet other embodiments, the diagnostic composition is used in the prediction of functional recovery after revascularization in patients with chronic ischemic left ventricle (LV) dysfunction.

In accordance with the present invention, the diagnostic composition may be used to determine blood flow to the heart muscle, for determining the effects of a heart attack, or myocardial infarction, on areas of the heart, to identify areas of the heart muscle that would benefit from a procedure such as angioplasty or coronary artery bypass surgery (in combination with a myocardial perfusion scan) or to map normal heart function.

The diagnostic composition, radiopharmaceutical or compound of the invention may be used either in vivo or in vitro for the purposes defined herein.

The diagnostic composition, radiopharmaceutical or compound of the invention may be used in the preparation of kits suitable for use in the diagnosis of a disease or disorder as defined herein.

In a further of its aspects the present invention provides a method for the diagnosis of a disease or disorder, said method comprising administering to a subject (human or non-human) suffering from or having predisposition to suffer from or having symptoms which may be associated with the disease or disorder, a diagnostically effective amount of a compound of Formula (I), as defined herein, or a radiopharmaceutical as defined herein or a diagnostic composition as defined herein, and imaging the body or any part of the body of said subject.

In some embodiments, the disease or disorder is coronary artery disease, as defined herein.

As use herein the term "diagnostically effective amount" refers to an amount of the compound, radiopharmaceutical or diagnostic composition, as defined herein, which allows for efficient molecular imaging depending on the type of the imaging technique (e.g. PET, SPECT etc) used, the acquisition parameters of the specific imaging technique used, the area of the body scanned, the physical condition of the subject, the purpose of the test or any other factors which are apparent to the person skilled in art.

In a still further aspect, the present invention provides a method of monitoring treatment of a subject, said method comprising administering to a subject having disease or disorder a compound as defined herein or a radiopharmaceutical, as defined herein, or a diagnostic composition, as defined herein, and measuring at least one imaging parameter associated with the disease or disorder in the subject using imaging of the body or any part of the body of said subject.

As used herein, the term "imaging parameter" refers to any parameter which can be measured using an imaging technique such as MPI, PET or SPECT as applied to the body or to any part of the body. Examples of such parameters include, inter alia, images (e.g. four-dimensional images or pictures of functional processes in the body) acquired by a nuclear medicine technician, a radiographer or a cardiac technician which correlate with myocardial vascular resistance, the extent of blood supply to the heart muscle (e.g. pointing to inadequate blood supply in specific regions of the heart), information about the heart's pumping function, the amount of scarring from a heart attack, the success of coronary bypass surgery or angioplasty.

A further method is provided, said method being for determining the severity of a disease or disorder, in a subject, the method comprising:

(i) obtaining at least one imaging parameter following the administration of at least one radiolabeled compound, as defined herein, or at least one radiopharmaceutical, as defined herein, or at least one composition, as defined herein, to a subject suffering from the disease or disorder, (ii) comparing the at least one imaging parameter obtained in (i) with a control reference that correlates with the severity of the disease or disorder, wherein the comparison allowing the determination of the severity of the disease or disorder in the subject.

In a further aspect, the present invention provides a method for determining the effectiveness of a therapeutic treatment of a disease or disorder in a subject, said method comprising:

(i) obtaining at least one imaging parameter following the administration, at a first time point, at least one radiolabeled compound, as defined herein, or at least one radiopharmaceutical, as defined herein, or at least one composition as defined herein, to the subject suffering from a disease or disorder, (ii) comparing the at least one imaging parameter obtained in (i) with at least one imaging input parameter obtained, following the administration, at a second time point, of at least one radiolabeled compound as defined herein or at least one radiopharmaceutical as defined herein or at least one composition as defined herein, to the subject suffering from the disease or disorder, and wherein the comparison allowing the determination of the effectiveness of a therapeutic treatment.

When PET is used for imaging, a dedicated PET or PET/CT scanner may be used. However, in accordance with the present invention it is also possible to acquire PET images using a conventional dual-head gamma camera fitted with a coincidence detector.

In some other embodiments, the methods of the invention are employed for determining the site of disease. In other embodiments, the methods of the invention are employed for measuring or quantifying or studying pharmacokinetics, biodistribution and drug interactions.

In some embodiments, the radiolabeled compound of the invention is conjugated to at least one drug; the uptake of the conjugate, the tissues in which it concentrates, and its eventual elimination, may be monitored using a molecular imaging technique such as MPI, PET or SPECT, as explained herein.

The present invention further provides methods for the synthesis of compounds of the invention, methods for the preparation of compositions of the invention, methods of administering to a subject of compositions of the inventions.

BRIEF DESCRIPTION OF THE FIGURES

In order to understand the invention and to see how it may be carried out in practice, numerous examples are provided and should be considered as non-limiting of the invention as disclosed.

FIGS. 4A-C show CT/PET of rats following tracer administration. Transaxial/coronal slices of CT/PET scans obtained 30 minutes after injection of [$^{11}$C]-1 (FIG. 4A) to a rat placed in a supine position under the scanner and [$^{11}$C]-2 (FIG. 4B) or [$^{11}$C]-3 (FIG. 4C), to a rat placed in a prone position under the scanner. The heart, marked with the crossed lines, can be detected in the CT, PET, and fused image.

FIGS. 6A-F provide representative microPET/CT coronal (FIGS. 6A, D), axial (FIGS. 6B, E) and sagittal (FIGS. 6C, F) slice images of the first 10 min summation of radioactivity distribution, following injection of [$^{11}$C]-4 (FIGS. 6A-C) and [$^{13}$N]NH$_3$ (FIGS. 6D-F) into rats.

DETAILED DESCRIPTION OF THE INVENTION

The present invention is based on the finding that radiolabeled ammonium salt derivatives can be used for the imaging of myocardial blood flow. They are positively charged, enhancing their tendency to undergo renal rather than hepatic excretion and increasing their tendency for cardiac accumulation. In addition, their lipophilicity can be easily manipulated via their functional groups and their labeling with carbon-11 is simple, straightforward and easily automated.

Furthermore, carbon-11's half-life (20.4 min) provides adequate time for chemical transformations and an option for delivery to surrounding PET centers while keeping the waiting period between consecutive scans to less than two hours, even for equal doses.

The labeled ammonium derivatives of the invention were synthesized and evaluated as myocardial blood flow PET imaging agents. [$^{11}$C]-2 gave high accumulation and retention in the heart, undergoing fast clearance mainly via the kidneys and yields high % ID/g heart ratios versus organs that interfere with cardiac imaging (e.g., blood, liver and lungs). In addition, since most tracers of this type are excreted via the kidneys and not the liver, the likelihood of gut activity (a well-known source of serious image quality problems that occur while using $^{99m}$Tc-labled lypophilic cations) interfering with myocardial imaging is minimal. [$^{11}$C]-3 gave superior cardiac accumulation, but its slower washout profile from the bloodpool, and lungs may pose a problem as far as resolution and patient dosimetry are concerned. [$^{11}$C]-4 gave the best cardiac uptake and washout profiles with heart/tissue ratios improving over time and giving the best overall results.

The biodistribution data for [$^{11}$C]-1 (log P=−3.92)[35] indicates little, if any, accumulation of tracer in the target tissue. Substitution of one methyl group in [$^{11}$C]-1 to the more lipophilic phenyl group in [$^{11}$C]-2 (log P=−2.74) [17], significantly increased cardiac activity uptake. This small, yet important, change in chemical structure increased cardiac uptake with minimal changes of the biodistribution profile to other organs. After lipophilicity was shown to play a major role in tracer uptake, the issue of increased positive charge was examined. The incorporation of the para-dimethylamino group into [$^{11}$C]-2 resulted in [$^{11}$C]-3-(log P=−0.93±0.1, n=3, data not shown). In addition, [$^{11}$C]-3 accumulated in the lungs to a higher degree, increasing background radioactivity. The switch of a second methyl with a phenyl in [$^{11}$C]-4 increased cardiac uptake but, more importantly, decreased cardiac washout to almost nothing, increasing heart/tissue ratios over time.

Figure 1:
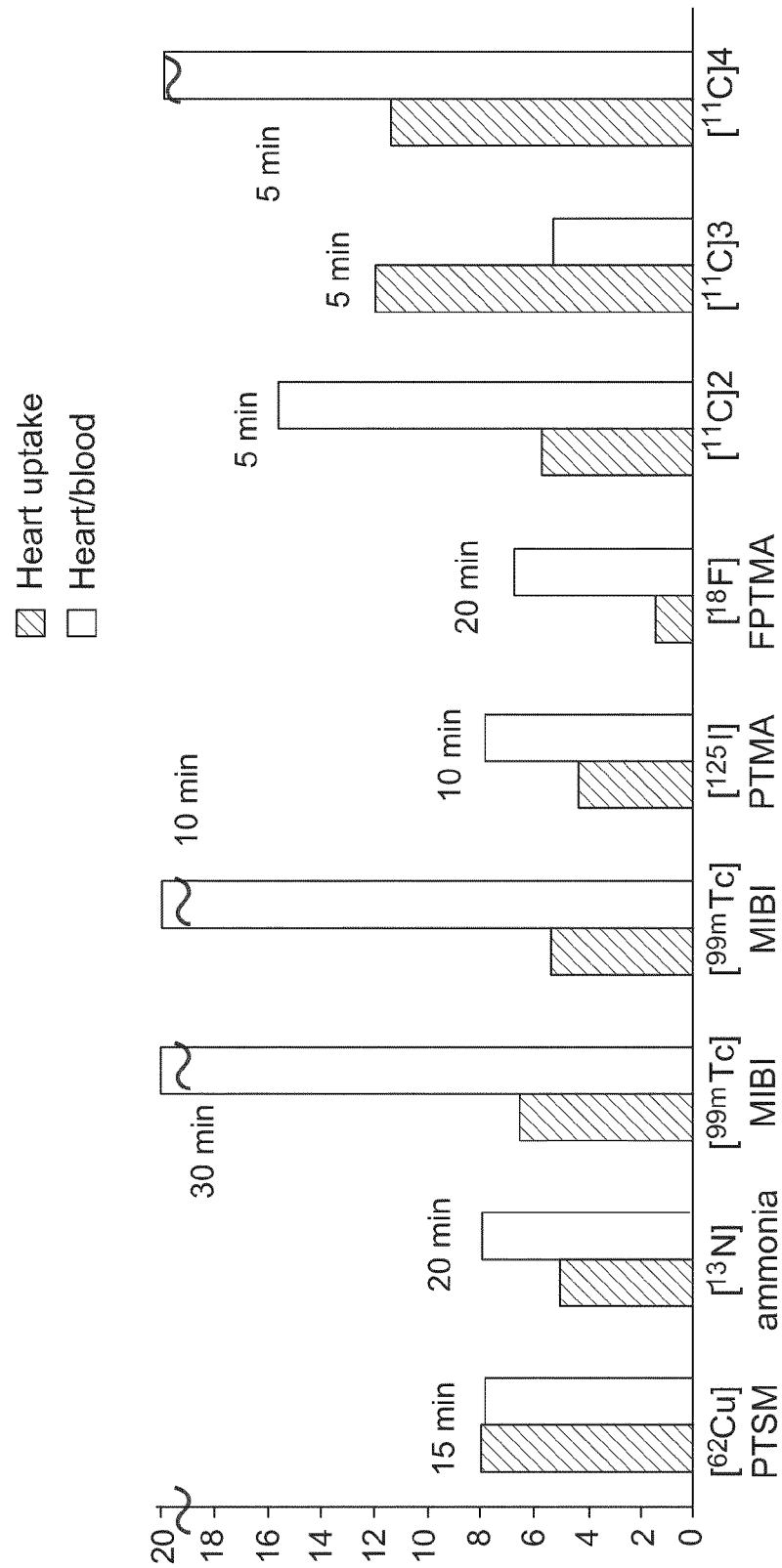
FIG. 1 shows the biodistribution data relating to experimental and clinically approved tracers. The [$^{99m}$Tc]MIBI on the left is taken from literature while that on the right is based on experiments performed in accordance with the invention. Data for all compounds except for the [$^{99m}$Tc]MIBI experiment and compounds [$^{11}$C]-2-[$^{11}$C]-4 performed in accordance with the invention was taken from Studenov et al. [10]. Heart uptake is expressed as a standard uptake value (percentage of radioactivity concentrated in the heart divided by the myocardial percentage of total body mass)

The results obtained with [$^{99m}$Tc]MIBI correlate with those from earlier publication (FIG. 1). This correlation validates the comparison of [$^{11}$C]-2 and [$^{11}$C]-4 results with the clinical and experimental tracers described in FIG. 1. Both compounds have heart uptake values which match or surpass those of well known MPI tracers such as [$^{99m}$Tc]MIBI and [$^{13}$N]ammonia and their heart/blood ratios exceed those of all other tracers except those of [$^{99m}$Tc]MIBI. The differences between the three ammonium salts [$^{125}$I]IPTMA, [$^{18}$F]FPTMA and [$^{11}$C]PTMA ([$^{11}$C]-2) are also notable. [$^{11}$C]-2 gave the highest heart uptake and heart/blood ratio followed by the results obtained with [$^{125}$I]IPTMA and [$^{18}$F]FPTMA respectively (FIG. 1).

The results of the PET/CT experiments in rats are consistent with the biodistribution results in mice. [$^{11}$C]-1 gave little cardiac accumulation while [$^{11}$C]-2 and [$^{11}$C]-3 both accumulated in the heart, indicating, once again, the potential of [$^{11}$C]-2 as a myocardial blood flow PET tracer. Accumulation of [$^{11}$C]-3 in the lungs and liver was higher than that observed with [$^{11}$C]-2 while the differences in cardiac washout profiles were negligible.

Materials and Methods

All solvents were of analytical grade. Dry acetonitrile was purchased from Merck (Darmstadt, Germany). Trimethylamine in THF 1M was purchased from Acros (Geel, Belgium). LiAlH$_4$ in THF (0.25M) was purchased from ABX (Radeberg, Germany).

Radiosynthesis was carried out on an automated module (GE, Munster Germany). $^{11}$C-carbon dioxide was produced by the $^{14}$N(p,α)$^{11}$C nuclear reaction on nitrogen containing 0.5% oxygen, using an 18/9 IBA cyclotron. At EOB, the target gas was delivered and trapped by a cryogenic trap in the [$^{11}$C]CH$_3$I module.

Radiochemical purity, chemical purity and identification of [$^{11}$C]-1 was performed on a Varian 9012Q HPLC system with an Alltach 550 conductivity detector and a PMT/Scintillator detector Bioscan flow count. A cation exchange IC-PAK™ Cation M/D 150*3.9 mm (Waters Corporation, Milford, Mass.) column was used with 5 mM HCl as eluent at a flow rate of 1.2 mL/min.

For the purification and analysis of [$^{11}$C]-2, two HPLC systems were used: (A) a reversed-phase system employing a Machery-Nagel 100-7 C-18 column (250×16 mm) and 15% EtOH/85% acetate buffer 0.1 M/pH 3.8 as eluent, at a flow rate of 8 mL/min which was installed in the [$^{11}$C]CH$_3$I module. (B) Analysis of formulated radiotracer was performed on the same Varian HPLC system as for [$^{11}$C]-1 employing a Varian 9050 UV-VIS detector instead of a conductivity detector and using a Waters μBondapak C-18 column (10 μm, 125 A, 300×3.9 mm) with 42% CH$_3$CN/58% acetate buffer 0.1 M/pH 3.8 as eluent at a flow rate of 1 mL/min.

For the purification and analysis of [$^{11}$C]-3, two HPLC systems were used: (C) a reversed-phase system employing the same preparative column as for [$^{11}$C]-2 with 30% EtOH/70% phosphate buffer 0.1M/pH 5.5 as eluent, at a flow rate of 8 mL/min which was installed in the [$^{11}$C]CH$_3$I module. (D) Analysis of formulated radiotracer was performed on the same Varian HPLC system with the same column as for [$^{11}$C]-2 with 85% CH$_3$CN/15% acetate buffer 0.1 M/pH 3.8 as eluent at a flow rate of 1 mL/min.

The purification of [$^{11}$C]-4 was performed in a similar manner to that of [$^{11}$C]-2 and analysis was done on the same equipment setup but the eluent used was a mixture of CH$_3$CN and acetate buffer 0.1 M/pH 3.8 with a gradient of 10-20% CH$_3$CN over a period of 10 minutes followed by another 10 minutes of 20% CH$_3$CN.

For the purification and analysis of [$^{11}$C]-6, two HPLC systems were used with the same equipment and conditions used for the synthesis of the labeled trimethyl-phenyl-ammonium iodide ([$^{11}$C]-2). The retention time (RT) of [$^{11}$C]-6 on preparative HPLC was 13 min and on analytical HPLC RT was 8.6 min. For the purification and analysis of [$^{11}$C]-7 and [$^{11}$C]-4, the same two systems as for [$^{11}$C]-2 were used with modifications made only to the eluents. Both compounds were purified on a preparative HPLC system with 15% EtOH/85% acetate buffer 0.1 M/pH 3.8 with a flow rate of 13 mL/min and RT=14-16 min. Both compounds were analyzed using a gradient of 10-20% acetonitrile/90-80% acetate buffer 0.1 M/pH 3.8 over 25 min, followed by 80% acetonitrile/20% acetate buffer for another 5 min. Flow was 1 mL/min for both compounds with [$^{11}$C]-7 and [$^{11}$C]-4 having a RT of 20 min and 22 min, respectively.

UV-VIS detectors were set to a wavelength of 254 nm in all the HPLC procedures.

Evaluation of THF, acetonitrile and ethanol traces in the final product solution was performed on a Varian Star 3400 CX gas chromatograph system with a TCD detector, a Bondapak Q80/100, 8 inch column and a helium gas phase at a flow rate of 40 mL/min.

BALC/c Ola/Hsd male mice (7-8 weeks, 25-30 g), SD/Hsd male rats weighing 250-275 g and NZW male rabbit weighing approximately 3.7 Kg were obtained from Harlan Industries, Inc. All animal studies were conducted under a protocol approved by the Animal Research Ethics Committee of the Hebrew University of Jerusalem and in accordance with its guidelines Animals were routinely kept in 12-h light/dark cycles and provided with food and water ad libitum.

Chemistry

Trimethyl-phenyl-ammonium iodide (Compound 2)

N'N'-Dimethylaniline (500 mg, 4.12 mmol) was dissolved in dichloroethane (2 mL) and methyl iodide (880 mg, 6.2 mmol) was added dropwise. The reaction was refluxed for 1 hour during which the product sedimented. The reaction was cooled to room temperature, the solid was filtered out, washed with dichloromethane and dried overnight in a desiccator to give 505 mg (90% yield). $^1$H NMR (DMSO-d6): δ7.95 (d, J=8.1, 2H), 7.5-7.7 (m, 3H), 3.59 (s, 9H); MS (ESI, m/z): 136 (M$^+$).

(4-Dimethylamino-phenyl)-trimethyl-ammonium iodide (Compound 3)

N,N,N',N'-Tetramethyl-benzene-1,4-diamine (200 mg, 1.22 mmol) was dissolved in dichloroethane (2 mL) and methyl iodide (173 mg, 1.22 mmol) was added dropwise. The reaction was refluxed for 1 hour, cooled to room temperature, the solid filtered out, washed with dichloromethane, dissolved in methanol and purified via flash column chromatography using a gradient of 0-8% MeOH:DCM to give 260 mg of grey solid (70% yield). $^1$H NMR (DMSO-d6): δ7.67 (d, J=9.3, 2H), 6.77 (d, J=9.3, 2H) 3.49 (s, 9H), 2.92 (s, 6H); MS (ESI, m/z): 179 (M$^+$).

Dimethyl-diphenyl-ammonium iodide (Compound 4)

Methyl-diphenyl-amine (756 mg, 4.13 mmol) was dissolved in dichloroethane (2 mL) and methyl triflate (1017 mg, 6.2 mmol) was added dropwise. The reaction was refluxed for 2.5 hours and the solvent was evaporated to give a white solid which was purified via flash column chromatography using a gradient of 0-2% MeOH:DCM to give 1237 mg of white solid (yield 92%). $^1$H NMR (DMSO-d6): δ7.5-7.7 (m, 10H), 4.06 (s, 6H); MS (ESI, m/z): 198 (M$^+$).

Trimethyl-m-tolyl-ammonium iodide (Compound 6)

Dimethyl-m-tolyl-amine (556 mg, 4.12 mmol) was dissolved in dry dichloroethane (2 mL) and methyl iodide (880 mg, 6.2 mmol) was added dropwise. The reaction was refluxed for 1 h during which time sedimentation occurred. The reaction was cooled to room temperature, the solid filtered out, washed with dichloromethane, and dried overnight in a desiccator to give a white powder (809 mg, 72% yield). $^1$H NMR (DMSO-d$_6$): δ7.82 (s, 1H), 7.74 (d, J=8.5 Hz, 1H), 7.51 (t, J=8 Hz, 1H), 7.93 J=7.5 Hz, 1H), 3.59 (s, 9H), 2.42 (s, 3H); MS (ESI, m/z): 150 (M$^+$).

Trimethyl-naphthalen-1-yl-ammonium trifluoro-methane-sulfonate (Compound 7)

Dimethyl-naphthalen-1-yl-amine (705 mg, 4.12 mmol) was dissolved in dry dichloroethane (2 mL) and methyl triflate (880 mg, 6.2 mmol) was added dropwise. The reaction was refluxed for 2 h while the solution turned dark brown. The reaction was cooled to room temperature, dichloroethane replaced with dichloromethane and diethyl-ether added to cause precipitation. Precipitate was collected, washed with ether and dried in a desiccator to give a white powder (1.36 g, 94% yield). $^1$H NMR (DMSO-d$_6$): δ8.59 (d, J=9, 1H), 8.21 (t, J=10 Hz, 2H), 8.09 (d, J=8 Hz, 1H), 7.78 (t, J=7 Hz, 1H), 7.71 (t, J=7 Hz, 1H), 7.66 (d, J=9.5 Hz, 1H), 3.89 (s, 9H); MS (ESI, m/z): 186 (M+).

Compound [$^{11}$C]-1

Carbon-11 MeI was prepared as follows: [$^{11}$C]CO$_2$ (44 GBq, 1,000 mCi) was trapped at −160° C. The temperature of the cooling trap was increased to −20° C., and the activity was transferred by a stream of argon (40 mL/min) into the first reactor containing 300 μL of 0.25 N LiAlH$_4$ in THF at −50° C. After 90 s, the solvent was removed under reduced pressure. In this manner, approximately 66% of the activity was recovered. The reactor temperature was increased to 160° C., HI was added and [$^{11}$C]MeI was distilled (argon flow of 15 mL/min) through a NaOH column to the second reactor, containing trimethylamine 1 M in THF (0.3 mL, 0.3 mmol) and 300 μL of acetonitrile. After 1 min of distillation, an average of 493±46 mCi (n=4) was trapped in the second reactor at −15° C. The reactor was sealed and heated to 65° C. for 5 minutes and then the reaction temperature was raised to 80° C. under vacuum for one minute in order to evaporate volatiles. The crude product was diluted with water (2 mL) and transferred to a round bottomed flask containing more water (8 mL). This solution was loaded onto a Light CM cation exchange Sep-Pak (Waters Corporation, Milford, Mass.), washed with water (17 mL), dried, and the product was eluted with saline (5 mL) to give 304±47 mCi. Radiochemical yield was 55±8% decay corrected to EOB with a total synthesis time of 25 min, a specific activity of 3.6±0.5 Ci/μmole and radiochemical purity higher than 99% (n=4).

Compound [$^{11}$C]-2

[$^{11}$C]MeI was produced as described for [$^{11}$C]1 and distilled to the second reactor, containing N',N'-dimethylaniline (20 μL, 0.17 mmol) and 280 μL of acetonitrile. After 1 min of distillation, an average of 505±90 mCi (n=4) was trapped in the second reactor at −15° C. The reactor was sealed and heated to 80° C. for 5 minutes. At the end of the 5 minute reaction, the reaction temperature was raised to 100° C. under vacuum for one minute in order to evaporate volatiles. The crude product was diluted with EtOH:acetate buffer (7:3, 2 mL) and automatically injected to the HPLC (system A), rt=8 minutes. The labeled product (80±1.6 mCi) was collected in a flask and diluted with saline to give a final solution of the tracer in 1:9 EtOH:acetate buffer (pH 3.8). Radiochemical yield was 19%±1.6 decay corrected to EOB with a total synthesis time of 35 min, specific activity of 2.5±0.3 Ci/μmole and radiochemical purity higher than 99%.

Compound [$^{11}$C]-3

[$^{11}$C]MeI was produced as described for [$^{11}$C]-1 and distilled to the second reactor, containing N,N,N',N'-tetramethyl-benzene-1,4-diamine (20 mg, 0.12 mmol) and 280 μL of acetonitrile. After 1 min of distillation, an average of 500±60 mCi (n=4) was trapped in the second reactor at −15° C. The reactor was sealed and heated to 80° C. for 5 minutes. At the end of the 5 minute reaction, the reaction temperature was raised to 100° C. under vacuum for one minute in order to evaporate volatiles. The crude product was diluted with water (2 mL) and automatically injected to the HPLC (system C), rt=13 minutes. The labeled product (150±31 mCi) was collected in a flask and a sample was diluted with saline to give a final solution of the tracer in 1:9 EtOH:phosphate buffer (pH 5.5). Radiochemical yield was 52%±11 decay corrected to EOB with a total synthesis time of 40 min, specific activity of 3.3±0.5 Ci/μmole and radiochemical purity higher than 99%.

Compound [$^{11}$C]-4 Trifluoro Methane Sulfonate Salt

[$^{11}$C]MeOTF (53±3 GBq (n=3)) was trapped in a reactor containing methyl-diphenyl-amine (20 μL) and dry 2-butanone (280 μL) at −15° C. The reactor was sealed and heated to 80° C. for 5 min. At the end of the 5 min reaction, the reaction temperature was raised to 90° C. under vacuum for 1 min in order to evaporate volatiles. The crude product was diluted with an ethanol/acetate buffer (7:3, pH 3.8, 0.1 M) solution (2 mL) and automatically injected to the HPLC, RT=14 min. The labeled product (1.96±0.37 GBq) was collected in a flask and a sample was diluted with saline to give a final solution of the tracer in 1:9 EtOH/phosphate buffer (pH 5.5). Radiochemical yield was 13%±2% decay corrected to EOB with a total synthesis time of 36 min, specific activity of over 260 GBq/μmol, and radiochemical purity higher than 99%.

Compound [$^{18}$F]-5

An [$^{18}$O]H$_2$O/[$^{18}$F$^-$] (29±4 GBq, n=4) mixture was trapped and transferred to a reactor through an ion exchange column (preactivated with 0.8 mL of EtOH and 3 mL of HPLC water) by elution with 0.5 mL of potassium carbonate (6 mg/mL). Following the addition of Kryptofix 2.2.2 solution (15 mg, 40 μmole in 1 mL CH$_3$CN), azeotropic removal of water and acetonitrile was achieved by heating the reactor to 100° C. under a stream of nitrogen for 3 min and under vacuum for another 1 min. Methanesulfonic acid 2-diphenylamino-ethyl ester (10 mg, 34 μmole) dissolved in CH$_3$CN (1 mL) was added, the reactor temperature was increased to 120° C. and the reaction mixture was stirred for 20 min. Volatiles were evaporated at the same temperature After cooling the mixture to under a stream of nitrogen for 1 min and under vacuum for another 2 min. The reactor was cooled to 50° C. and then 2,6-di-tert-butyl-4-methylpyridine (92 mg, 0.45 mmol) in dry dichloromethane (400 μL) and methyl trifluoro-methanesulfonate (50 μL, 0.44 mmol) in dry dichloromethane (200 μL) were added. The reactor temperature was increased to 105° C. for 25 min. and then cooled to 45° C.

Non-decay corrected radiochemical yields were approximately 85% and 80% for the first and second steps of the synthesis, respectively.

Purification was performed either via normal phase seppak (preactivated with 5 mL dichloromethane) using 2% MeOH in dichloromethane which was evaporated and replaced with saline or by replacing the dichloroethane with 70% EtOH in acetate buffer (pH 3.8, 0.1 M) and purification via preparative HPLC using 10% EtOH in acetate buffer (pH 3.8, 0.1M) as eluent. The product was analyzed using HPLC with a flow of 1 mL/min and a gradient of 30-90% CH$_3$CN (70-10% acetate buffer, pH3.8, 0.1M) over 40 minutes.

Compound [$^{11}$C]-6

The production of [$^{11}$C]methyl iodide ([$^{11}$C]MeI) was described in detail in the past.[3, 11] 20±1.5 GBq (n=4) of [$^{11}$C]MeI were trapped in a reactor containing dimethyl-m-tolyl-amine (20 μL) and dry acetonitrile (280 μL) at −15° C. The reactor was sealed and heated to 80° C. for 5 min. At the end of the 5-min reaction, the reaction temperature was raised to 90° C. under vacuum for 1 min in order to evaporate volatiles. The crude product was diluted with an ethanol/acetate buffer (7:3, pH 3.8, 0.1M) solution (2 mL) and automatically injected into the HPLC RT=13 min. The labeled product (3.1±0.36 GBq) was collected in a flask and a sample was diluted with saline to give a final solution of the tracer in 1:9 EtOH/phosphate buffer (pH 5.5). Radiochemical yield was 27%±3 decay corrected to EOB with a total synthesis time of 37 min, specific activity of 100±11 GBq/μmol, and radiochemical purity higher than 99%.

Compound [$^{11}$C]-7

[$^{11}$C]MeI was distilled through silver trifluoro-methanesulfonate column heated to 200° C. using a Helium flow of 15 mL/min and [$^{11}$C]MeOTf (21±1 GBq (n=3)) was trapped in a reactor containing N'N'-dimethyl-1-naphtylamine (20 μL) and dry 2-butanone (280 μL) at −15° C. The reactor was sealed and heated to 80° C. for 5 min. At the end of the 5-min reaction, the reaction temperature was raised to 90° C. under vacuum for 1 min in order to evaporate volatiles. The crude product was diluted with an ethanol/acetate buffer (7:3, pH 3.8, 0.1 M) solution (2 mL) and automatically injected into the HPLC, RT=16 min. The labeled product (1.6±0.24 GBq) was collected in a flask and a sample was diluted with saline to give a final solution of the tracer in 1:9 EtOH/phosphate buffer (pH 5.5). Radiochemical yield was 14%±2 decay corrected to EOB with a total synthesis time of 40 min, specific activity of over 170 GBq/μmol, and radiochemical purity higher than 99%.

Radiochemistry

Quality Control

Three quality control tests were performed parallel to each other:

A GC injection of 5 μL was performed to ensure a maximal concentration of THF, acetonitrile and ethanol below 720 ppm, 410 ppm and 10% v/v, respectively.

Two HPLC injections were prepared: a 50 μL injection for radiochemical purity and specific activity calculations and a 50 μL co-injection with a non-radioactive standard to insure the tracer's identity. pH was checked as well using a pH strip in the appropriate range of the expected solution.

Animal Studies

Tracer Biodistribution Studies in Mice

Compounds [$^{11}$C]-1, [$^{11}$C]-2, [$^{11}$C]-3, [$^{11}$C]-4, [$^{11}$C]-6, [$^{11}$C]-7 and Technetium-99 m methoxy isobutyl isonitrile ([$^{99m}$Tc]MIBI) biodistribution studies were carried out with BALB/c Ola/Hsd mice (7-8 week). Tracers were injected in a 10% EtOH/saline solution as vehicle. Either [$^{11}$C]-1 (62±15 μCi; 2.4±6 MBq; 122±13 μL), [$^{11}$C]-2 (68±12 μCi; 2.5±0.4 MBq; 188±1.3 μL), [$^{11}$C]-3 (70±17 μCi; 2.6±0.6 MBq; 185±5 μL), [$^{11}$C]-4 (18±5 μCi; 666±185 MBq; 195±2.2 μL or 1.24±0.93 MBq, 229±63 μL), [$^{11}$C]-6 (1.95±0.21 MBq, 83±41 μL), [$^{11}$C]-7 (2.01±0.16 MBq, 169±73 μL) or [$^{99m}$Tc] mibi (14.2±1.7 μCi; 3.6±0.4 MBq; 97.7±12.5 μL) were injected via the lateral vein. At allotted time points (1, 5, 10, 15 min), blood was drawn from the orbital sinus, mice were sacrificed by cervical dislocation and selected organs (heart, lungs, liver and kidney) were excised, weighed and measured for their radioactive content using a γ-counter (1480 Wizard 3"). Distribution of activity was calculated as the percentage of injected dose per gram of organ (% ID/g). Activity uptake ratios of various organs were calculated by dividing the corresponding calculated % ID/gs.

Similar to the biodistribution studies in mice, [$^{11}$C]-4 was injected into male SD/Hsd rats (293±9 g) in a 10% EtOH/saline solution (3.1±0.5 MBq; 530±134 μL) via the lateral tail vein. At the allotted time points, blood was drawn, animals were sacrificed, and selected organs were excised, weighed and measured for their radioactive content.

Distribution of activity was calculated as the percentage of injected dose per gram of wet tissue (% ID/g). Activity uptake ratios of various organs were calculated by dividing the corresponding calculated % ID/g. Heart standardized uptake values (SUVs) were calculated by dividing the % ID in the heart of each rat by the percentage of heart weight of the total body weight of the animal.

PET/CT Imaging in Rat

All PET/CT studies were carried out with SD/Hsd male rats weighing 250-275 g. Rats were anaesthetized with Ketamine:Xylazine 2% (100 μL/100 g body weight injected i.p). Animals were placed in a supine ([$^{11}$C]-1) or prone ([$^{11}$C]-2 and [$^{11}$C]-3) position on a flat polystyrene foam support, with feet taped to minimize likelihood of movement during the scans. Imaging was performed on a Discovery ST PET/CT tomograph (General Electric, Milwaukee, Wis.), with intrinsic spatial resolution: in plane 6.2 mm, axial 5.0 mm. CT transmission scans started prior to administration of the tracer. PET scans started immediately with the IV administration of the tracer, approximately 300 μCi (11 GBq). Fifty minutes dynamic emission scans were obtained in 2D mode, and corrected for random counts, dead time, scatter and attenuation. Images were reconstructed using iterative reconstruction. Regions of interest (ROI) were drawn on the heart, lungs, liver, kidneys and bladder and time activity curves were calculated for these regions.

Micro-PET scans were also carried out using healthy Wistar rats (154±47 g). Anesthesia was induced, and thereafter maintained by 3% and 1%-2.5% isoflurane in $O_2$, respectively. During the scans, rats were maintained normothermic using a heating blanket. All CT and PET acquisitions were carried out using the Inveon™ multimodality PET-CT small animal-dedicated scanner (Siemens Medical Solutions USA Inc.). Rats were positioned in the scanner so that the heart was in the center of the field of view. Following a CT scan, PET list-mode acquisition was started at the time of injection of [$^{11}$C]-4 (14.3±5.7 Mbq/rat, n=4) or [$^{13}$N]—$NH_3$ (81.1±20.4 Mbq/rat, n=6) in the lateral tail vein. Acquisitions continued for 60 min or 40 min post-injection, for [$^{11}$C]-4 or [$^{13}$N]—$NH_3$, respectively.

The list-mode emission scans were sorted into 29 (6×10, 8×30, 5×60, 10×300 sec) and 24 (12×10, 6×30, 5×300, 1×600 sec) dynamic frames, for [$^{11}$C]-4 and [$^{13}$N]—$NH_3$ respectively. Emission sinograms were normalized and corrected for attenuation, dead time and decay. Image reconstruction was performed using Fourier rebinning and two dimensional ordered-subsets expectation maximization (2D-OSEM), with a voxel size of 0.776×0.776×0.796 mm$^3$.

Image analysis and quantification of radioactivity concentration in regions of interest (ROIs) were performed using Inveon Research Workplace 3.1 (Siemens Medical Solutions USA Inc.). Delineation of ROIs was performed by manual segmentation, and the corresponding time activity curves (TACs) were calculated.

PET/CT Studies of [$^{11}$C]-4 in a Porcine Model
Study Protocol

Following a constriction of the left circumflex coronary artery (LCxA) via insertion and manipulation of a stent, stress and rest dynamic-PET studies were performed in three pigs. Pigs underwent dynamic PET acquisition following injections of [$^{11}$C]-4 both at rest and under pharmacological stress [(207±30 MBq in 10±4 mL) and (203±11 MBq in 16±1 mL), respectively]. Images were acquired for each animal at rest and stress on the same day, allowing a minimum of 5 half-lives (approximately 2 h for carbon-11 and 1 h for nitrogen-13) in between injections to minimize crosstalk. Pharmacological stress was induced by an IV infusion of adenosine (500 μg×min$^{-1}$×kg$^{-1}$ body weight), beginning 3 min prior to injection of the tracers, and maintained for an additional 3 min. When necessary, hypotension was prevented by concomitant IV administration of dobutamine (2 μg×min$^{-1}$×kg$^{-1}$ body weight).

In the first two pigs, myocardial infarction developed as evidenced by either ECG monitoring or repeated angiography that demonstrated total stent occlusion. In order to prevent complete occlusion in the third pig, the angiography and stent insertion were carried out in the PET/CT room, thus minimizing the animal's movement, and the animal was given higher doses of heparin (a sum of 30,000 units throughout the experiment) based on Activated Clotting Time (ACT) test. In the third pig, the adenosine stress protocol was performed twice: once with [$^{13}$N]$NH_3$ (700 MBq in 1 mL) injection, and 2.5 h later, the adenosine stress protocol was repeated with [$^{11}$C]-4 injection.

Animal Preparation

To prevent blood clotting, pigs were treated with aspirin (250-300 mg) and plavix (150-300 mg) on the day before the procedure. On the day of the study, the animals were anesthetized using ketamine/xylazine (15 mg/kg/2 mg/kg) and Butorphanol 0.2 mg/kg IM as premedication. For induction, ketamin/diazepam (4 mg/kg/0.02 mg/kg) was administered intravenously. Animals were ventilated and anesthesia, maintained using isoflorane 2% inhalation (via tracheal tube). Animals were monitored continuously for ECG, body temperature, $O_2$ saturation, blood pressure, pulse and breathing. Vascular access was prepared in the left and right ear veins for drug and tracer administration, and a catheter was placed in the left femoral artery for stent insertion and arterial blood pressure measurements.

Partial Occlusion of the LCx Coronary Artery

Following anesthesia, the pigs underwent cannulation of the left femoral artery with a 7 Fr introducer sheath and a 7 Fr hockeystick catheter (Cordis) was positioned in the left main coronary artery. Partial LCx coronary artery occlusion was induced via partial inflation of the proximal component of a JOSTENT Graftmaster (Abbott Vascular, USA) inside the LCx coronary artery, creating a funnel-shaped structure. Before insertion of the stent, the 3.5×16 mm JOSTENT was partially crimped over a 3.5 mm balloon with its distal third beyond the inflating balloon. Inflation of the balloon dilates the crimped part leaving a distal cone that is not dilated with an orifice approximately 1 mm in diameter. Thus, when deployed in an artery that is 3.5 mm in diameter, a partial, yet significant stenosis was established.

Coronary angiography was performed with 20-30 mL of contrast media and 3.5 mm wide and >20 mm long segment of the LCx artery that was free of major branches. The stent system was brought to the assigned segment over a floppy 0.014 coronary wire (ASAHI). The balloon was inflated with a pressure of 14-16 atmospheres (10-15 seconds) and the balloon was then deflated and withdrawn. Angiography was then performed in two different projections to ascertain that the cone-shaped stent enabled preserved continuous flow through its patent distal orifice. To ensure partial stenosis rather than complete occlusion of the artery during the PET imaging, a repeated angiography was taken at the end of imaging.

PET/CT Acquisition

Animals were placed in a supine position with the heart in the center of the field of view of the PET/CT scanner. Imaging was performed on a Discovery ST PET/CT tomograph (GE Healthcare, Milwaukee, Wis.), with intrinsic spatial resolution: in-plane 6.2 mm, axial 5.0 mm. CT transmission scans were carried out prior to the administration of the tracer. Dynamic emission scans starting 10-15 seconds before tracer injection (4×5 secs, 15×3 secs, 5×5 secs, 7×30 secs, 2×2.5 mins, 6×5 min: 40 minutes total acquisition time for [$^{11}$C]-4; 12×10 secs, 6×30 secs, 3×5 mins: 20 mins total acquisition time for [$^{13}$N]$NH_3$) were acquired in a two-dimensional mode and corrected for random counts, dead time, scatter, and attenuation.

PET Data Analysis

Images were reconstructed using OSEM iterative reconstruction. The PET images were then visualized and analyzed using the Cardiac Image Analysis System Carimas 2.0 (Turku PET Centre, Turku Finland: http://www.turkupetcentre.net/carimasturku/) software. Using this software package, the long axis of the left ventricle is defined in transaxial slices through the heart; the heart is reoriented to the standard short axis projection, and volumes of interest (VOIs) are defined semi-automatically for the entire left ventricle and for the territories of the main blood vessels as well as smaller subdivisions, and for a blood pool region toward the base of the left ventricle. Time activity curves (TACs) were calculated for all these VOIs. In addition, VOIs for the right ventricle, and lungs were drawn on images obtained by summing all time frames from 10 min post-injection to the end of the scan, using IDL (Research Systems, Inc.). TACs were calculated for these VOIs as well. Myocardial tracer activity ratios between the myocardium (lateral wall) and the lung, and left ventricular blood pool were calculated.

In order to create standard stress and rest images, the dynamic data between 5 and 20 min of each imaging set were temporally summed for each reconstructed transaxial slice. Each transaxial set of images was processed with the help of commercial myocardial perfusion viewing software (Myovation-LVSD-GE Healthcare) in order to create short-axis, vertical long-axis and horizontal long-axis myocardial slices as well as corresponding polar maps.

Results

Chemistry

Both trimethylamine and tetramethylammonium iodide were purchased from commercial sources. Trimethyl-phenyl-ammonium iodide (2) was synthesized using N'N'-dimethylaniline and methyl iodide in dichloroethane (90% yield), requiring no purification procedure other than filtration and washing with dichloromethane. (4-Dimethylamino-phenyl)-trimethyl-ammonium iodide (3) was synthesized using N',N', N,N-tetramethyl-benzene-1,4-diamine and methyl iodide in dichloroethane and purified using flash column chromatography (70% yield). Dimethyl-diphenyl-ammonium iodide (4) was synthesized using methyl-diphenyl-amine and methyl triflate in dichloroethane and purified using flash column chromatography (90% yield).

The issue of charge density was investigated by adding a methyl group on the meta position on the phenyl ring of compound 2 to give compound 6. In order to investigate lipophilicity, the phenyl ring of compound 2 was replaced with a naphthalene moiety, producing compound 7. Since some of the lipophilic cationic tracers for MPI are based on a cationic core surrounded by lipophilic side chains, one of the methyl groups in compound 2 was replaced with a phenyl yielding compound 4. Ultimately, compounds 7 and 4 differ not only in their Log P values, but also in the distribution pattern of the lipophilicity around the cationic core.

Compound [$^{11}$C]-6 was synthesized in a similar manner to that of [$^{11}$C]-2 and gave a slightly improved decay corrected radiochemical yield (27%, EOB). Compounds [$^{11}$C]-7 and [$^{11}$C]-4 were synthesized employing the carbon-11 methylation reagent [$^{11}$C]MeOTf. Radiochemical yields for both compounds were significantly lower than those of the other ammonium tracers (14% and 13% for [$^{11}$C]-7 and [$^{11}$C]-4, respectively).

Radiochemistry

[$^{11}$C]-1 Synthesis

The synthesis of [$^{11}$C]-1 was based on the labeling conditions of [$^{11}$C]choline [30] with minor modifications. The methylation reaction was carried out in a THF/CH$_3$CN mixture (1:1) at 65° C. for 6 minutes. Volatiles were evaporated; the product was diluted with water, loaded onto a cation exchange Sep-Pak and then eluted with saline. This 25-minute radiosynthesis gave 304±47 mCi of [$^{11}$C]-1 with a radiochemical yield of 55% (decay corrected to EOB), specific activity of 3.6±0.65 Ci/µmole and 99% radiochemical purity. (n=4)

[$^{11}$C]-2 Synthesis

The methylation reaction to obtain [$^{11}$C]-2 was performed in CH$_3$CN at 80° C. for 5 minutes. Volatiles were evaporated, a solution of ethanol:acetate buffer (7:3) was added and the product purified using RP-HPLC (system A). This 35-minute radiosynthesis gave 80±1.6 mCi [$^{11}$C]-2 with a radiochemical yield of 19%±0.16 (decay corrected to EOB) a specific activity of 2.5±0.3 Ci/µmole and radiochemical purity of 99% (n=3).

[$^{11}$C]-3 Synthesis

The methylation reaction to obtain [$^{11}$C]-3 was performed as described for [$^{11}$C]-2 but after volatile evaporation, water was added and the product was purified using RP-HPLC (system C). This 40-minute synthesis gave 150±31 mCi of [$^{11}$C]3 with a radiochemical yield of 52%±11 (decay corrected to EOB) a specific activity of 3.3±0.5 Ci/µmole and radiochemical purity of 99% (n=3).

[$^{11}$C]-4 Synthesis

The methylation reaction to obtain [$^{11}$C]-4 was performed as described for [$^{11}$C]2 except for the use of a AgOTf column to produce the methyl triflate rather than methyl iodide for the methylation reaction. This 40-minute synthesis gave 19±2.4 mCi of [$^{11}$C]3 with a radiochemical yield of 7%±0.8 (decay corrected to EOB) a specific activity of 2.7±0.4 Ci/µmole and radiochemical purity of 99%. (n=3).

Biodistribution

Figure 2A:
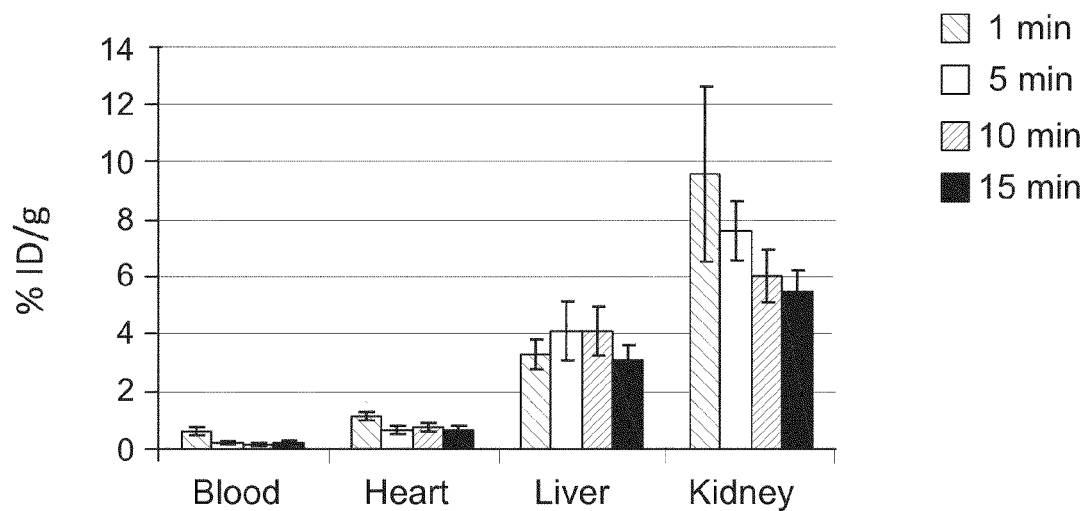
FIGS. 2A-E present radioactivity biodistribution in mice at 1, 5, 10 and 15 minutes post-injection of [$^{11}$C]-1 (FIG. 2A), [$^{11}$C]-2 (FIG. 2B), [$^{11}$C]-3 (FIG. 2C), [$^{11}$C]-4 (FIG. 2D) and [$^{99m}$TC]MIBI (FIG. 2E). BALB/c Ola/Hsd mice (n=4 per time point) were injected with the tracer and sacrificed at four different time points following injection of the tracer. Organs were excised and weighed, and their radioactivity content was measured with a γ-counter. Activity uptake is expressed as the mean % ID/g±SEM.

The in-vivo biodistribution of [$^{11}$C]-1, [$^{11}$C]-2, [$^{11}$C]-3, [$^{11}$C]-4, [$^{11}$C]-6, [$^{11}$C]-7 and [$^{99m}$Tc]MIBI was evaluated in mice at different time points post-injection. The biodistribution of radioactivity 1, 5, 10 and 15 minutes post-injection is presented in FIG. 2, expressed as the percentage of the total injected dose per gram of tissue (% ID/g). For compound [$^{11}$C]1, the highest activity levels were observed in the liver and kidneys, with activity accumulation in the heart reaching only 0.7-1.1% ID/g (FIG. 2A). Cardiac uptake was 3 and 9 folds lower than in the liver and kidneys, respectively, and surpassed blood activity by less than 6-fold (FIG. 3A).

Figure 2B:
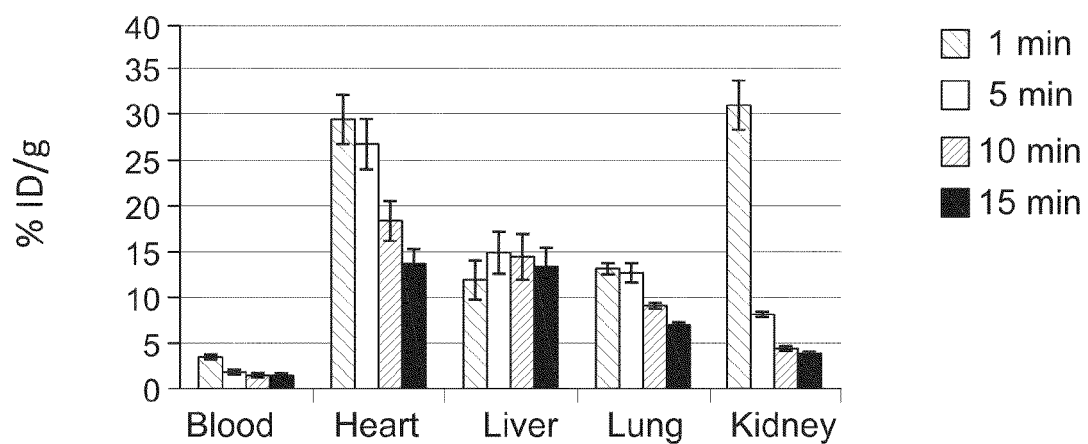
Figure 3A:
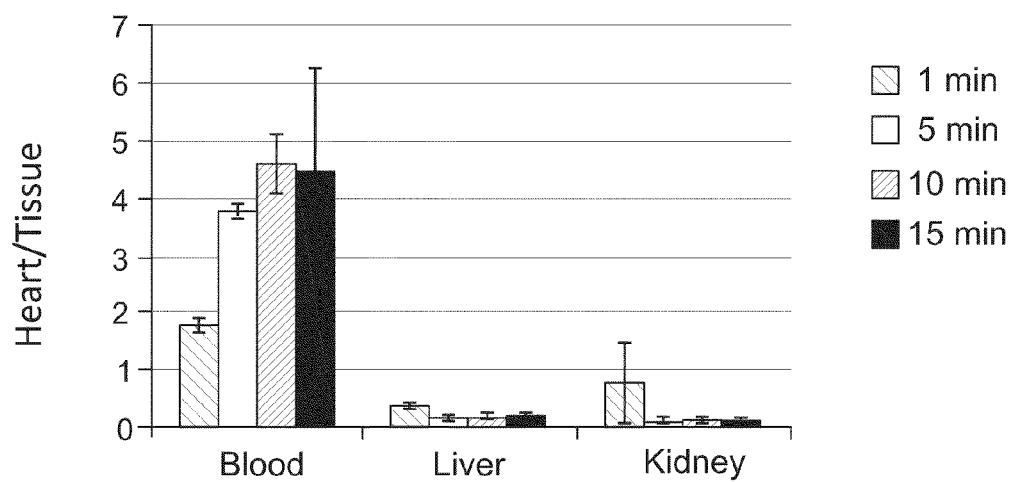
FIGS. 3A-E show the activity uptake ratios of the heart vs. liver, lung, kidney and blood compartments over a 15 minute period post-injection of [$^{11}$C]-1 (FIG. 3A), [$^{11}$C]-2 (FIG. 3B), [$^{11}$C]-3 (FIG. 3C), [$^{11}$C]-4 (FIG. 3D) and [$^{99m}$TC]MIBI (FIG. 3E).
Figure 3B:
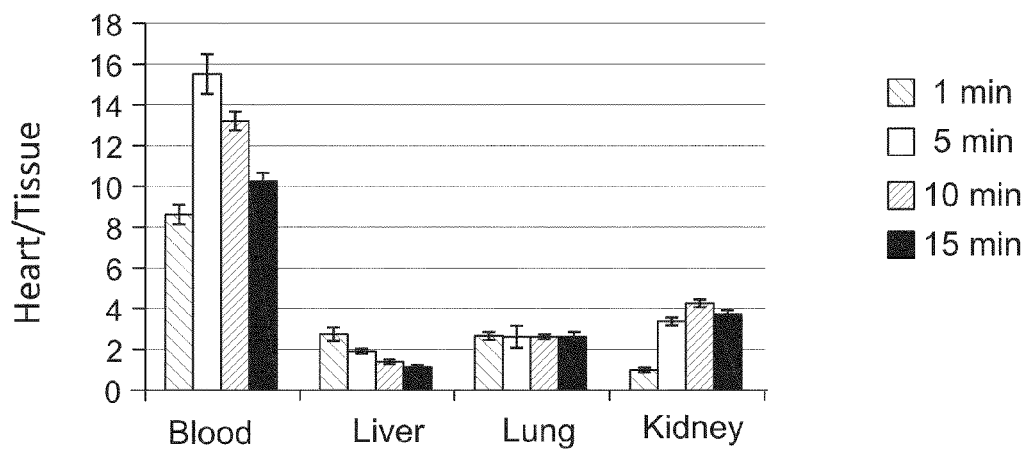

For compound [$^{11}$C]-2 the radioactivity in the heart was the highest among the tissues examined, reaching 29.5%, 26.8%, 18.5% and 13.9% ID/g at 1, 5, 10 and 15 minutes post injection (FIG. 2B). Tracer accumulation in the heart was seemingly at its highest 1 minute after administration, but this is due, in part, to moderate radioactivity levels in the blood which resides in the heart's vessels and chambers. Optimal heart/blood activity uptake ratios were obtained with [$^{11}$C]-2 at 5 and 10 minutes post-injection (15.5- and 13.3-fold, respectively, FIG. 3B). The time window of 5-10 minutes gave good activity uptake ratios of heart to blood, liver and lungs (15.5, 1.9 and 2.6, at 5 minutes post injection, respectively).

Figure 2C:
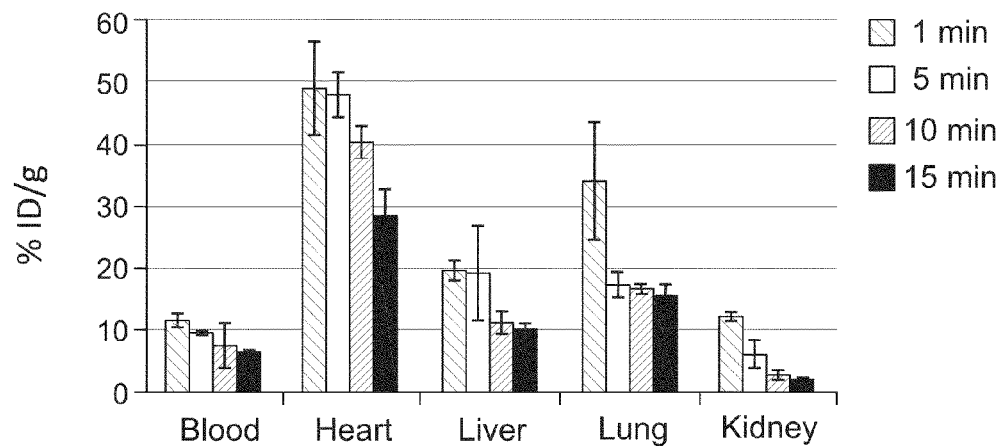
Figure 3C:
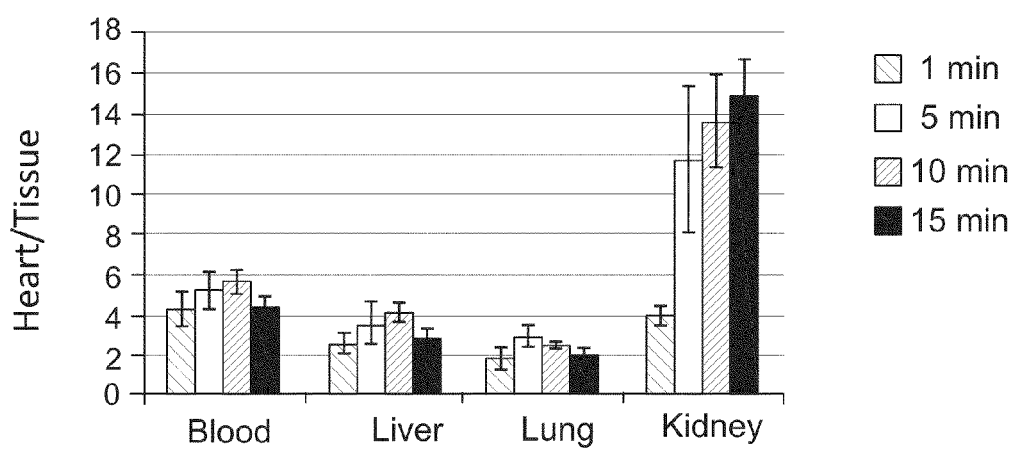

[$^{11}$C]-3 was synthesized with the idea that its increased charge in physiological pH could enhance its cardiac uptake and accelerate renal filtration and excretion. Indeed radioactivity uptake values in the heart increased to 48.7%, 47.7%, 40.15% and 28.5% ID/g at 1, 5, 10 and 15 minutes post injection, respectively (FIG. 2C). In addition, both liver and renal washout profiles were accelerated, leading to higher heart/kidney and heart/liver ratios (FIG. 3C). However, slower activity washout from blood pool and increased activity uptake in lungs were observed. The slow washout of [$^{11}$C]-3 from the blood pool lowered the heart/blood activity uptake ratio in comparison with [$^{11}$C]-2 (5.6-versus 16-fold, FIGS. 3C and 3B). Examination of later time points post injection of the tracer (30 and 60 minutes, data not shown) revealed decreased ratios of activity uptakes and could not compensate for the slow blood activity washout profile.

[$^{11}$C]-4 was synthesized to evaluate what effects a further increase in log P will have on the cardiac uptake and retention of the ammonium tracer in the heart. The change not only increased heart uptake at all time points to 46.6%, 50.4%, 62.5% and 44.5% at 1, 5, 10 and 15 minutes but decreased radioactivity washout from the heart almost completely. This change did not change liver uptake of the tracer significantly but decreased lung uptake and the activity washout from the blood washout occurred faster. This tracer showed the best heart/blood activity uptake ratios (44 and 61 fold at 5 and 10 minutes respectively)

Figure 2D:
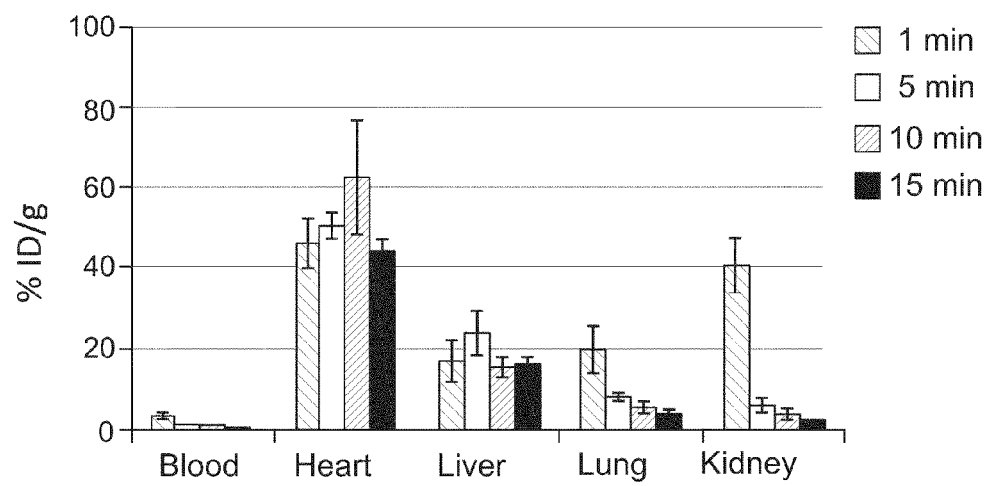
Figure 2E:
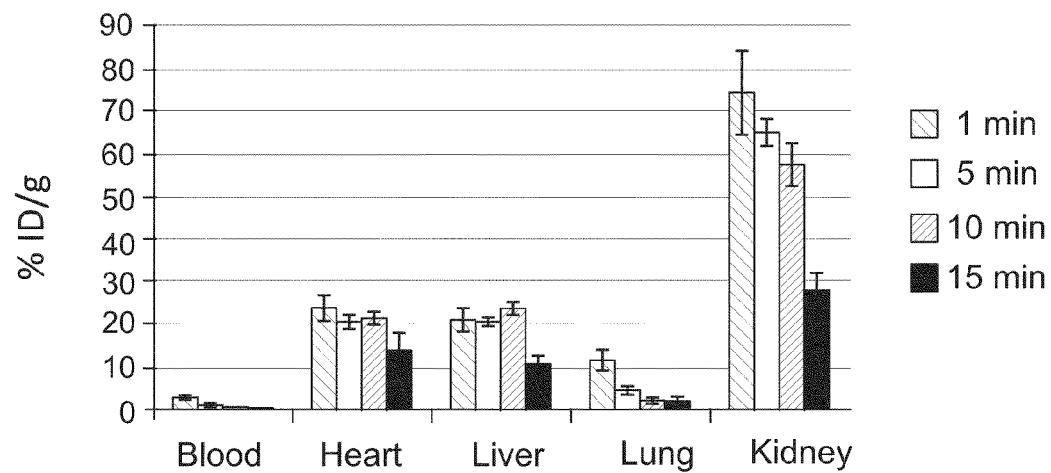
Figure 3D:
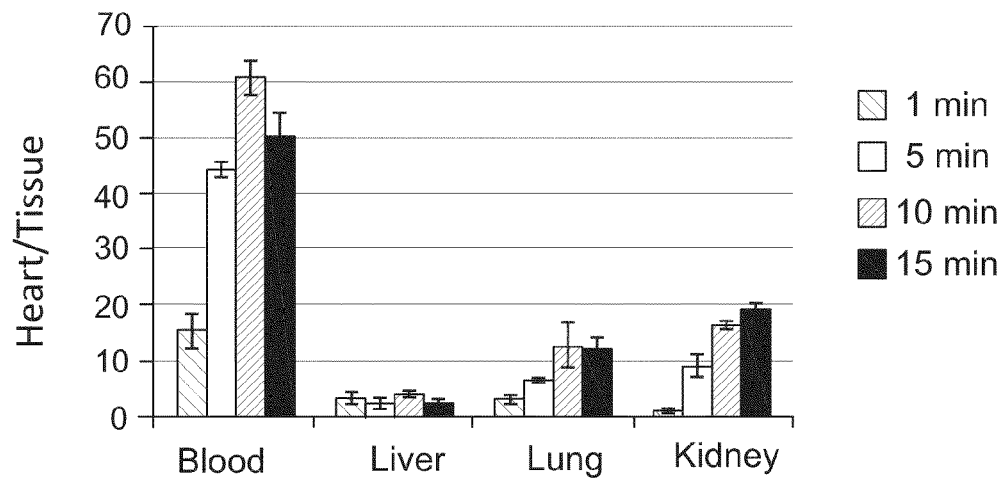
Figure 3E:
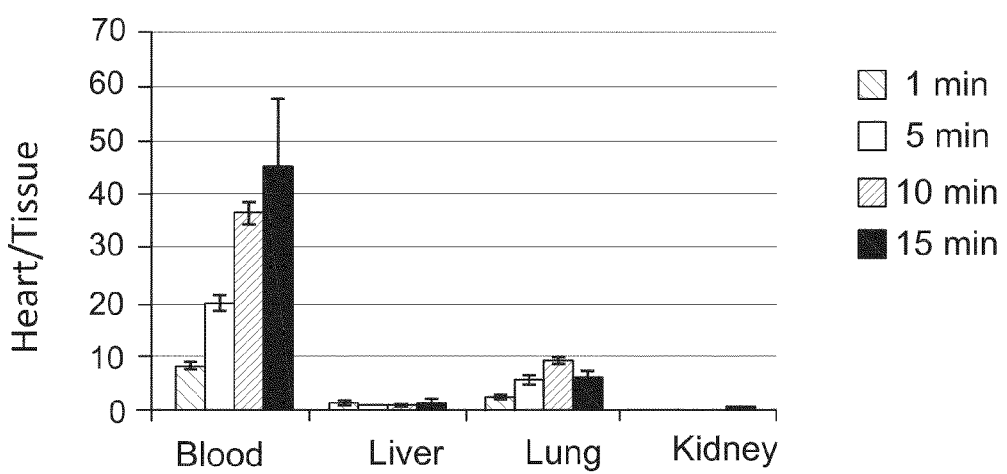

The four ammonium-based tracers' biodistribution profiles were compared with those of the well known myocardial perfusion imaging tracer [$^{99m}$Tc]MIBI at the same time points. Radioactivity accumulation in the heart was modest, reaching 24%, 20.5% 21.4% and 13.8% ID/g at 1, 5, 10 and 15 minutes post injection, respectively (FIG. 2D). However, due to rapid clearance from the blood pool, heart/blood activity uptake ratios obtained with [$^{99m}$Tc]MIBI were relatively high reaching to 45.1-fold at 15 minutes post injection (FIG. 3D). Accumulation of activity in the liver was average, but with the decreased activity in the heart, heart/liver ratios were lower than those obtained with [$^{11}$C]-2, [$^{11}$C]-3 and [$^{11}$C]-4.

[$^{11}$C]-2 (n=7) and [$^{11}$C]-6 (n=8) have very similar biodistribution profiles with cardiac % ID/g reaching ~20% and heart/blood ratios reaching ~13 at 10 min post injection (results not shown). Despite this similarity, it is evident that at each time point and in almost all parameters, [$^{11}$C]-6 surpasses [$^{11}$C]-2. [$^{11}$C]-6 has lower uptake in the lungs and higher uptake in the heart, leading to improved heart/tissue ratios. [$^{11}$C]-7 (n=4) has improved heart uptake (~33% ID/g, 10 min) with little effect on uptake in other organs or blood pool clearance. This provides improved heart/tissue ratios in all tissues, at all time points. Despite these advantages, similarly to [$^{11}$C]-2, there is still considerable washout of activity from the heart and heart/blood ratios do not exceed 20. [$^{11}$C]-4 (n=6) gave the best results of all compounds. Its heart uptake was constant at ~50% ID/g at all observed time points and its blood pool clearance was faster than that of all the other tracers. In addition, although liver uptake was increased, kidney uptake did not change significantly and lung uptake decreased. Due to the minimal washout of tracer from the heart, heart/tissue ratios improved over time, suggesting the feasibility of performing MPI/PET imaging with this compound at later time points. Finally, 4 was compared to the popular SPECT agent, [$^{99m}$Tc]-MIBI. [$^{99m}$Tc]-MIBI (n=4) showed a better blood pool clearance and slightly lower lung uptake. However, heart uptake of [$^{11}$C]-4 was twice as high, while kidney retention was significantly less than that obtained with [$^{99m}$Tc]-MIBI. [$^{11}$C]-4 had better heart/tissue ratios for all organs, at all time points. Heart SUV was calculated, and reached a value of 9.7±0.5 at 15 min post injection.

Figure 5A:
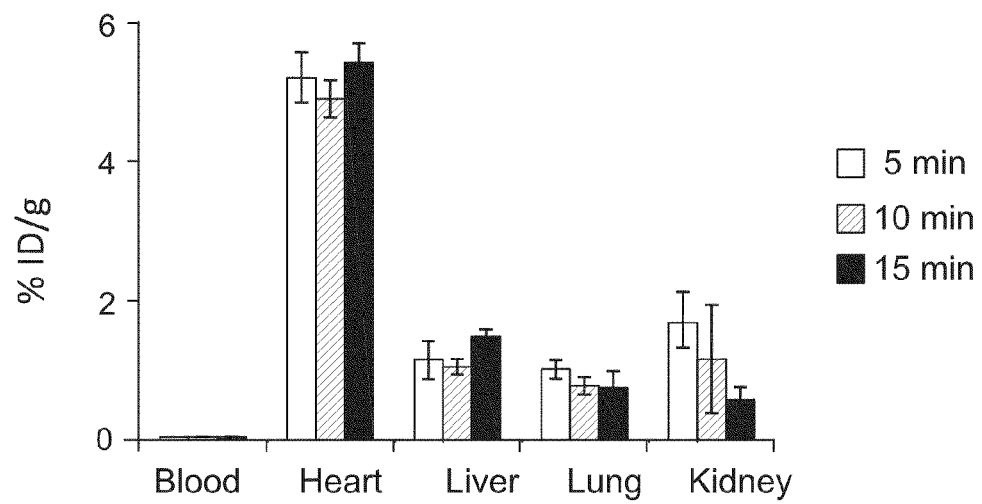
FIGS. 5A-B demonstrate the radioactivity distribution (FIG. 5A) and heart/tissue activity uptake ratios (FIG. 5B) following administration of [$^{11}$C]-4 into rats.
Figure 5B:
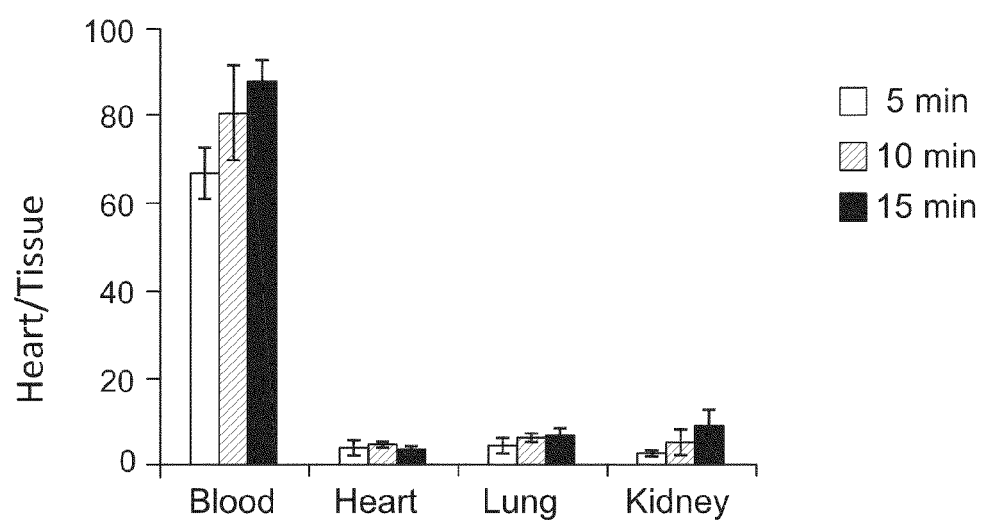

The in vivo distribution of [$^{11}$C]-4 in rats was evaluated at 5, 10 and 15 min post-injection of the compound (n=3 per time point). As shown in FIGS. 5A and 5B, radioactivity uptake values in the heart were consistent throughout the first 15 min, reaching a value of approximately 5% ID/g. In contrast, high clearance from blood pool was observed, yielding a heart/blood activity ratio of about 90, at 15 min post injection. At the same time point, approximately 5-fold higher levels of radioactivity were measured in the heart compared to the lungs, kidneys and the liver. Heart SUV at 15 min post injection was 15.6±0.4.

PET/CT Scans in Rats

The feasibility of cardiac blood flow imaging with the three tracers was evaluated using SD/Hsd male rats Animals were anesthetized, placed under a clinical PET/CT scanner, injected with approximately 300 µCi for rats and imaged for up to 50 minutes. FIG. 4 shows a comparative PET study between [$^{11}$C]-1, [$^{11}$C]-2 and [$^{11}$C]-3 in rats. The presented images were obtained at 30 minutes post-injection. In both [$^{11}$C]-2 and [$^{11}$C]-3 the heart is clearly visible along with the kidneys and bladder while with [$^{11}$C]-1 the heart is not visible and activity uptake accumulation is observed mainly in the liver and bladder.

microPET in Rats

FIGS. 6A-F illustrate the summation of radioactivity distribution throughout the first 10 min after injection of [$^{11}$C]-4 (FIGS. 6A-C) and [$^{13}$N]NH$_3$ (FIGS. 6D-F). The myocardium could be clearly visualized with either compound, although a better contrast was obtained using [$^{11}$C]-4.

Figure 7A:
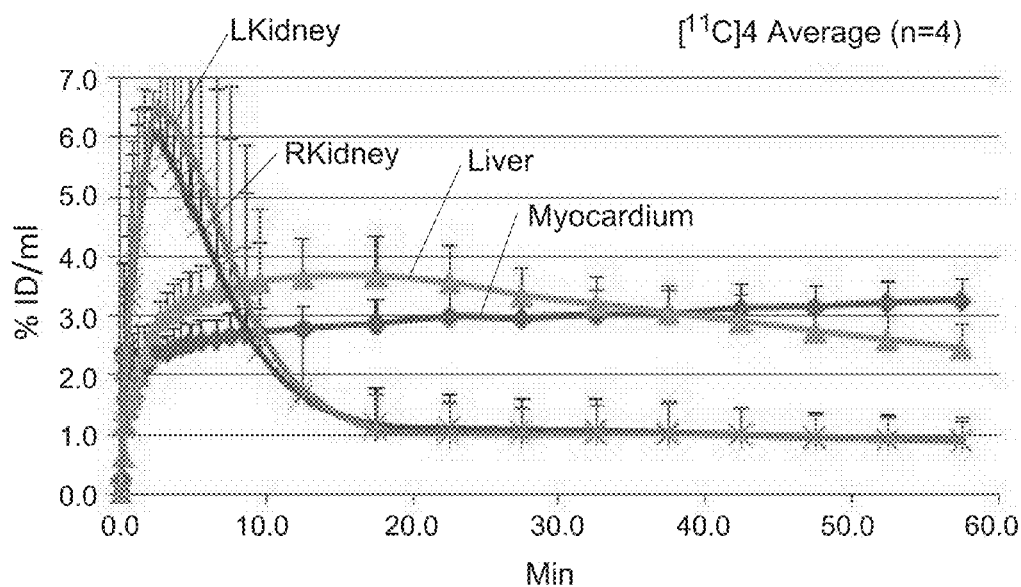
FIGS. 7A-B are microPET time activity curves of selected organs following injection of [$^{11}$C]4 (FIG. 7A) and [$^{13}$N]NH$_3$ (FIG. 7B) into rats.
Figure 7B:
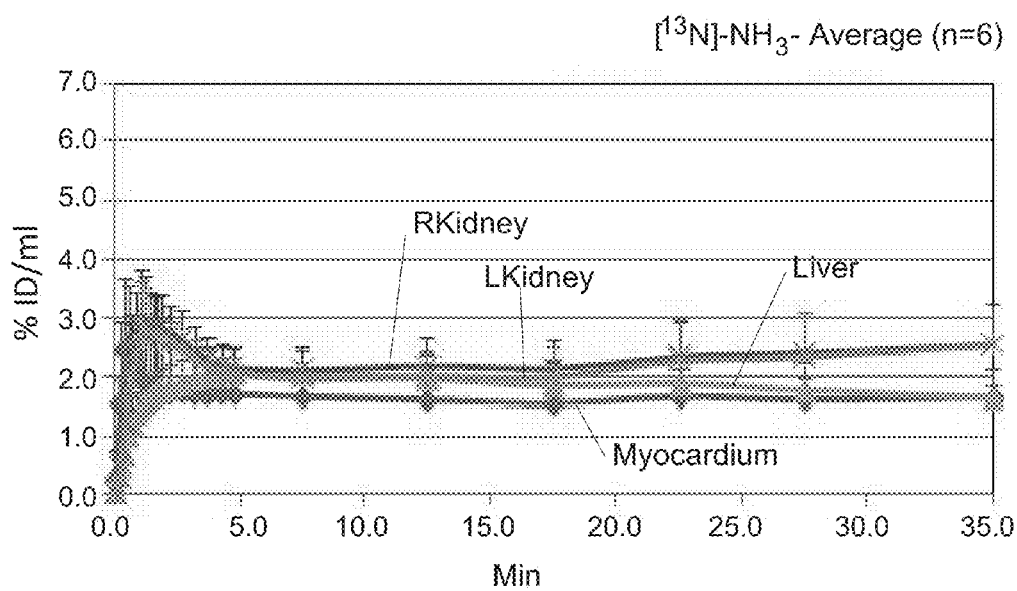

Time activity curves obtained after injection of [$^{11}$C]-4 (n=4) and [$^{13}$N]NH$_3$ (n=6) into rats were calculated for organs of interest. As demonstrated in FIGS. 7A-B, the myocardial radioactivity uptake after injection of [$^{11}$C]-4 was steady, reaching a value of ~3% ID/mL within a few min after injection. In comparison, radioactivity concentrations in the myocardium following injection of [$^{13}$N]NH$_3$ did not exceed 1.7% ID/mL, and were somewhat inconsistent over time. When comparing radioactivity uptake levels in the kidneys, [$^{11}$C]-4 reached an initial peak value of 6% ID/mL, compared to a corresponding value of 3% ID/mL for [$^{13}$N]NH$_3$. While kidney uptake rapidly declined during time for [$^{11}$C]-4, reaching ~1% ID/mL at 20 min after injection, a significantly smaller decline was observed for [$^{13}$N]NH$_3$. Lastly, higher levels of radioactivity were measured in the liver following administration of [$^{11}$C]-4 compared to [$^{13}$N]NH$_3$, although radioactivity was cleared more rapidly from the liver for the former.

PET Imaging of Ischemia and Infraction in Pigs Using [$^{11}$C]-4

For the evaluation of [$^{11}$C]-4 uptake during ischemia in a large-animal model, pigs rather than dogs and rabbits, were chosen for two main reasons: first, similarities between porcine and human cardiovascular physiology, heart size and anatomy, and the distribution of coronary perfusion make them superior models compared to other species. Second, pigs' coronary arteries are large enough to better enable the catheterization techniques required for our model of partial coronary occlusion. This novel model simulating significant, albeit partial coronary artery occlusion, has clear advantages over other models which rely on either permanent or transient complete occlusions. Our model is more realistic since MPI tracers are clinically used to evaluate and stratify patients with chronic CAD, and obviously the expected tracer kinetics in such patients vary radically between partial and complete occlusion. The first pig underwent stent insertion and angiography as described in the methods section. An additional angiography, performed at the end of imaging, showed that the stent caused complete occlusion. Rest and stress images with [$^{11}$C]-4 showed a very severe, non-filling defect (FIG. 8), compatible with myocardial infarction.

Figure 9:
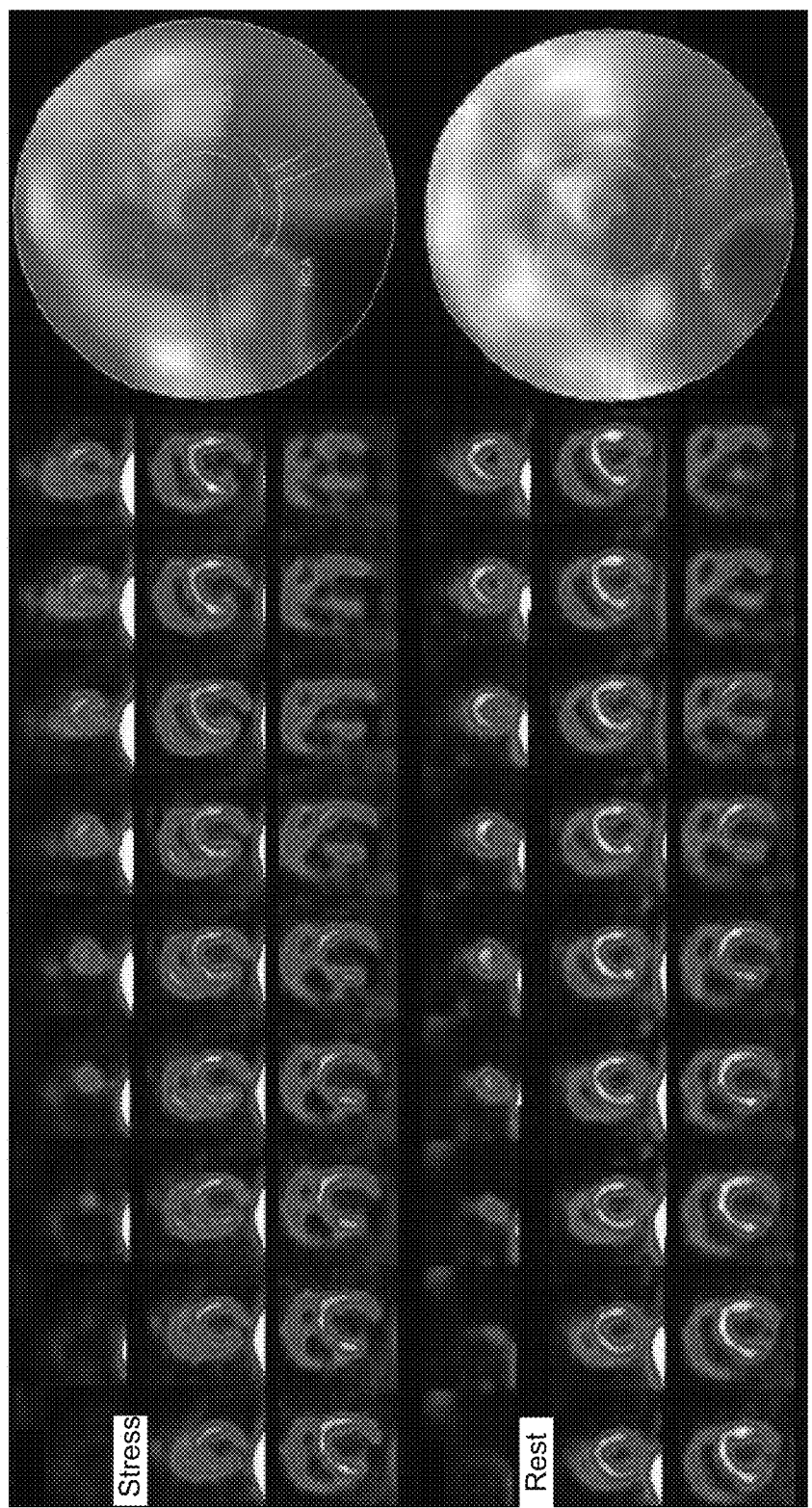
FIG. 9 shows the short axis slices and polar maps of [$^{11}$C]-4 at stress (top) and rest (bottom) obtained between 5 and 20 min in the second pig.

The second pig, shortly after stent insertion, developed an acute coronary syndrome with inferior wall ST-elevation and eventually development of corresponding q waves in the same leads compatible with myocardial infarction. Since ECG was so conclusive, it was deemed unnecessary to perform angiography after the imaging studies. Once again, images (FIG. 9) show fixed, severe inferior wall defect with partial filling-in of the inferolateral wall. Upon realizing the tendency of the inserted stent to clot immediately, several precautions were taken for the third pig experiment. The animal underwent angiography and stent insertion in the PET scanner room to minimize damage to the occluded artery during animal transport and the animal received a much higher dose of anticoagulants reaching a much higher activated clotting time (ACT). ECG monitoring throughout the experiment was normal and repeated angiographies at the end of imaging and in between rest and stress imaging showed no clotting and an opened, yet narrowed stent, with preserved coronary perfusion during contrast injection.

Figures 10A, 10B, 10C:
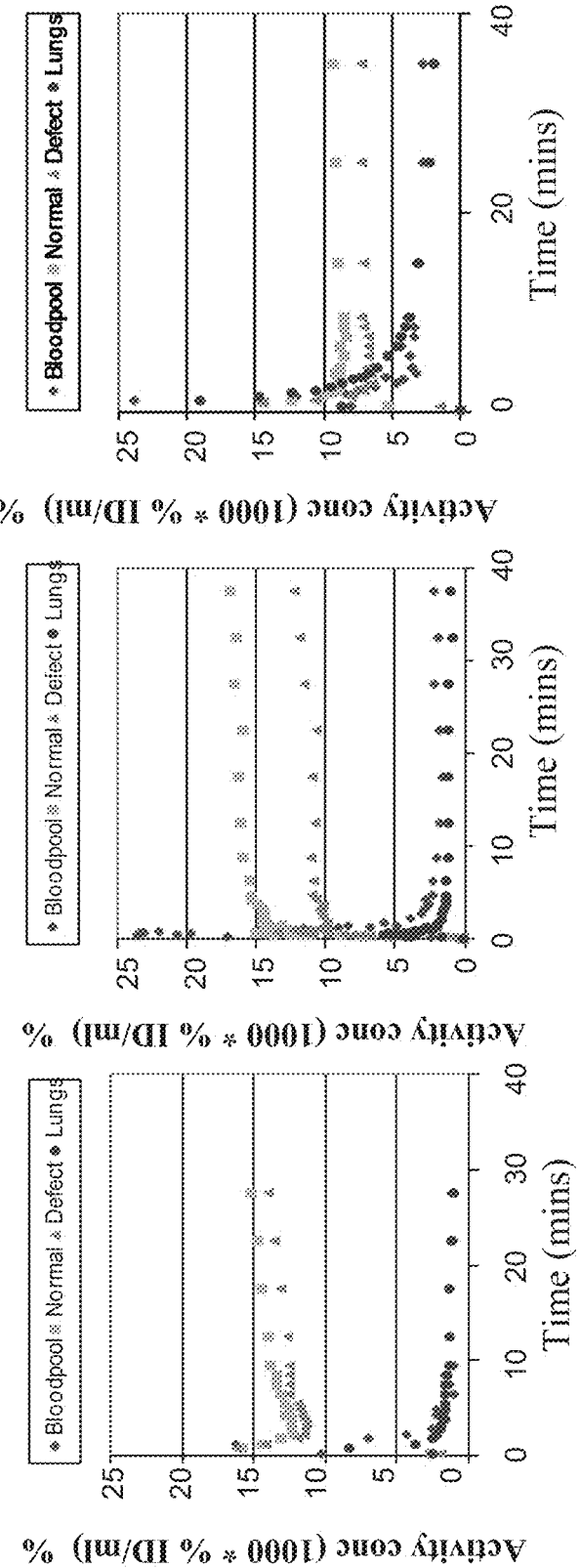
FIG. 10A-C are time activity curves of selected organs of [$^{11}$C]-4 injected to an ischemic pig model during rest (FIG. 10A) and stress (FIG. 10B) and of [$^{13}$N]NH$_3$ during stress (FIG. 10C), third pig.

Time-activity curves in pig 3 (TACs, FIGS. 10A-C) demonstrate the pharmacokinetic characteristics of [$^{11}$C]-4 that were basically quite similar to those observed in rats with MicroPET (FIG. 7). Cardiac accumulation is fast and reaches a plateau approximately 10 min after injection. Lung accumulation is minimal and washout of activity from the blood pool is rapid (reaching a minimum after 5 min). The initial decrease of activity in the volume of interest marked as "normal myocardium" viewed in the first few minutes is probably due to "spill-over" from the high activity in the blood inside the ventricular cavity. The ratio between the uptake in the normal and the ischemic areas stays rather constant throughout the scanning period indicating minimal tracer re-distribution. A similar pattern is noted on adenosine stress after [$^{13}$N]NH$_3$ injection, with two differences—first, normal myocardial uptake as "% injected dose" is higher for [$^{11}$C]-4 than for [$^{13}$N]NH$_3$, second, the myocardial/blood pool and myocardial/lung uptake ratios are higher for [$^{11}$C]-4.

Figure 8:
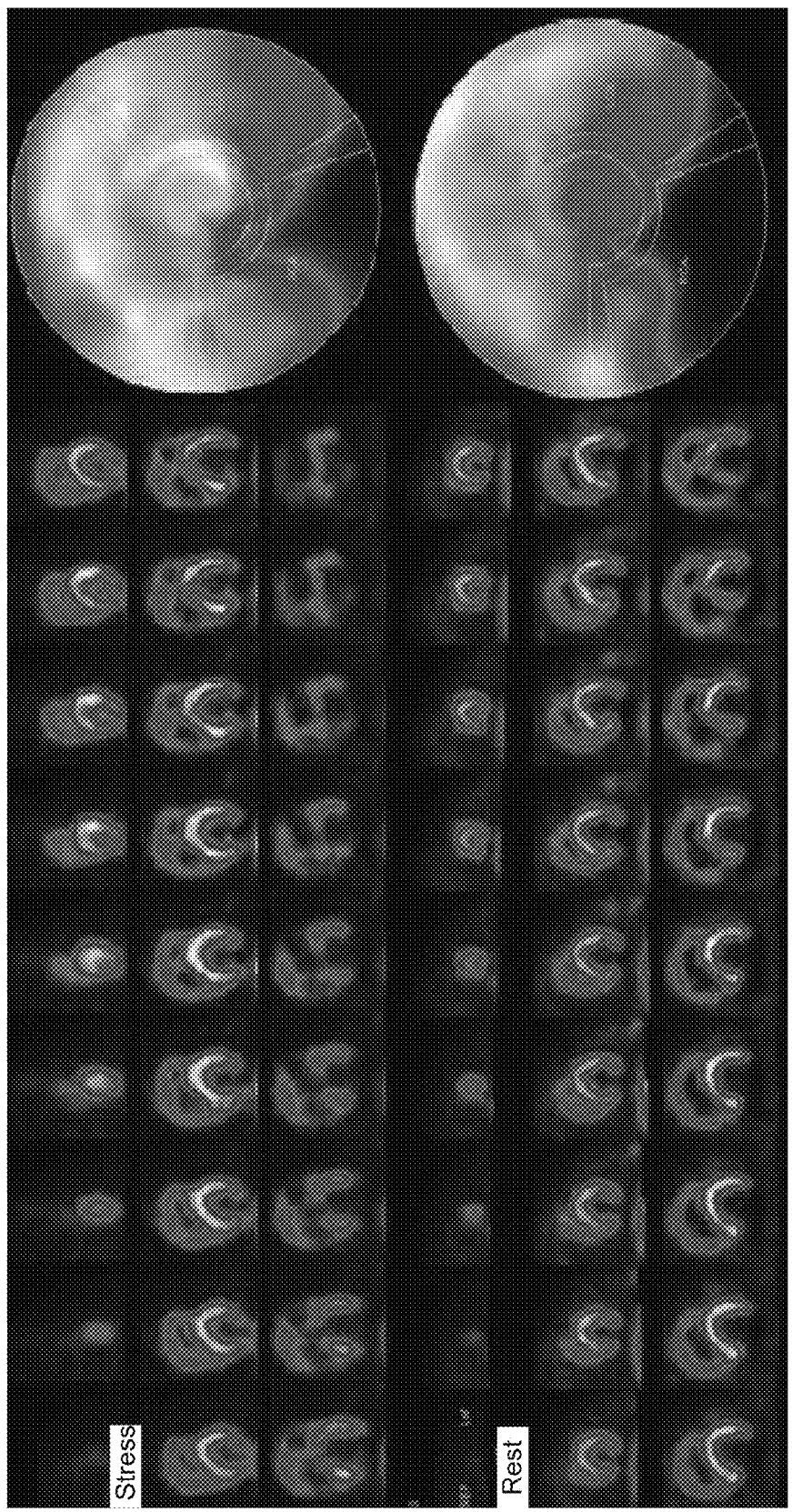
FIG. 8 shows the short axis slices and polar maps of [$^{11}$C]-4 at stress (top) and rest (bottom) obtained between 5 and 20 min in the first pig.

The images of pig 1 (FIG. 8) show a very severe and fixed defect in the left ventricular inferior wall, consistent with a myocardial infarction imaging pattern. Indeed, complete stent occlusion was seen on repeated angiography following the imaging sessions. The defect is apparent in both rest and stress scans by the absence of uptake wherein only its edges undergo partial filling (FIG. 8). Following the dynamic scans, the animal underwent a whole body PET/CT scanning to evaluate biodistribution into organs located outside the field of view of dynamic acquisition.

The images of pig 2 (FIG. 9) show a severe and fixed defect in the left ventricular inferior wall, consistent with a myocardial infarction imaging pattern, while an inferolateral extension of the stress defect shows partial filling-in. In fact, pig 2 developed an acute coronary infarction shortly after stent insertion, as depicted in the ECG monitoring which shows inferior wall ST-elevation and eventually q waves developing in the same ECG leads.

Figure 11:
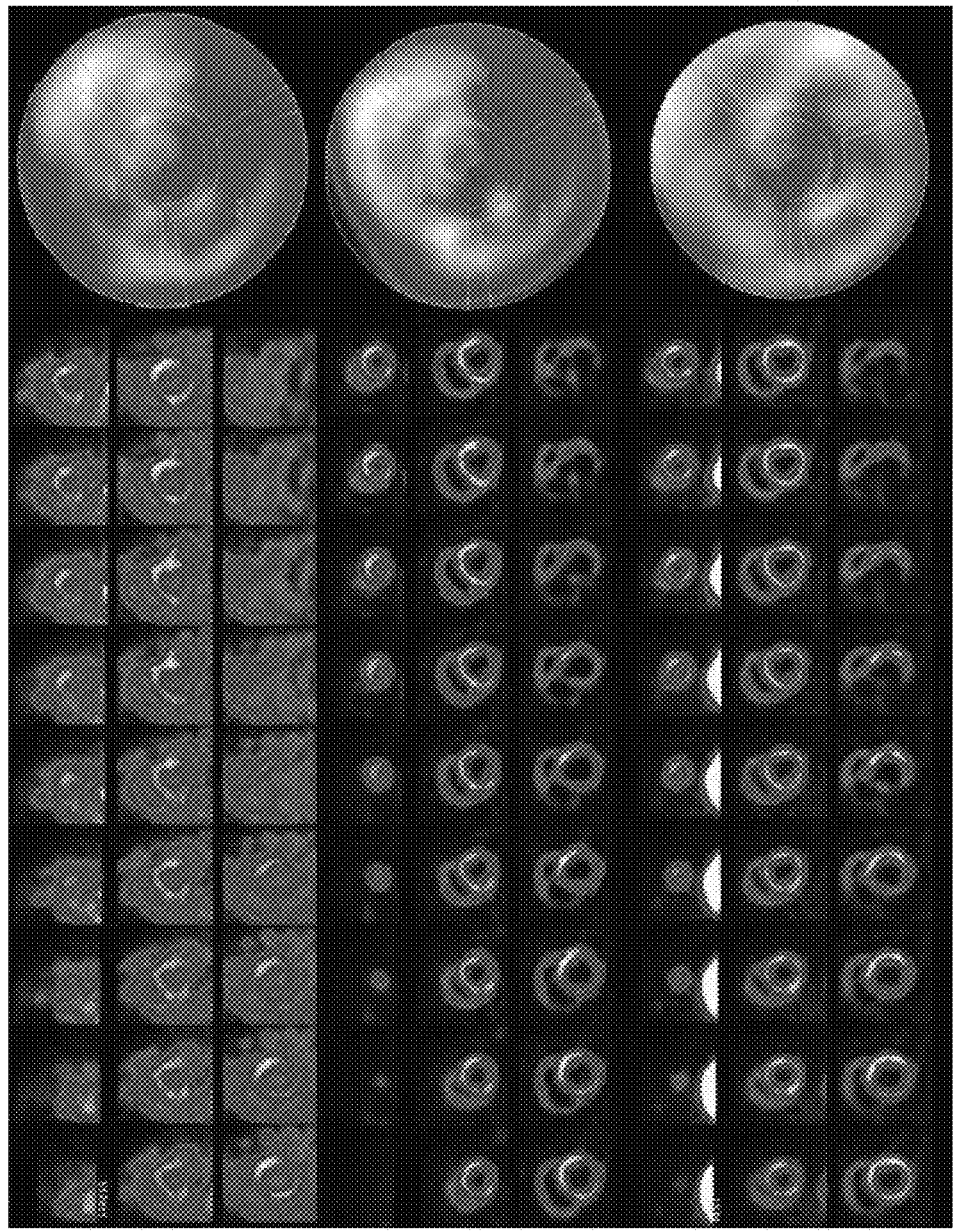
FIG. 11 shows the short axis representations and polar maps of [$^{13}$N]NH$_3$ at stress (top), [$^{11}$C]-4 at stress (middle), and [$^{11}$C]-4 at rest (bottom) obtained between 5 and 20 min in the third pig.

Adenosine stress images of pig 3 acquired separately after [$^{13}$N]NH$_3$ and [$^{11}$C]-4 injections both show a severe inferolateral defect (FIG. 11). Rest [$^{11}$C]-4 images show filling in of that defect compatible with the clinically sine qua non pattern of "reversible ischemia" typically noted during MPI in cases of significant, yet partial coronary artery stenosis. ECG monitoring throughout the experiment was normal and angiography at the end of imaging shows an opened, yet narrowed stent, with preserved coronary perfusion during contrast injection. In addition, the images obtained with [$^{11}$C]-4, look better compared to those obtained with [$^{13}$N]NH$_3$, notwithstanding the fact that the dose of [$^{13}$N]NH$_3$ injected was three-fold higher than that of [$^{11}$C]-4 dose. Higher contrast is noted between myocardium and blood pool, between myocardium and lung and between normal and ischemic myocardium on [$^{11}$C]-4 images compared with [$^{13}$N]NH$_3$. The better contrast between the heart muscle and its cavity even presents a clearer right ventricular silhouette despite the much higher dose of [$^{13}$N]NH$_3$ injected.

Summary

The addition of a methyl group on the aromatic ring of [$^{11}$C]-2 to create [$^{11}$C]-6 changes the partial charge density of the ammonium core. The minor improvement in biodistribution cannot be attributed solely to a change in Log P, since [$^{11}$C]-6's and [$^{11}$C]-4's have very similar C Log P (−1.59 and −1.47, respectively); yet [$^{11}$C]-4's measured parameters are incomparable. When the phenyl in [$^{11}$C]-2 was replaced with a naphthalene in [$^{11}$C]-7 (C Log P 0.92), the improvement in biodistribution parameters as well as cardiac uptake was substantial. Cardiac washout, however, did not change and heart/tissue ratios did not improve over time as is the case with [$^{99m}$Tc]-MIBI. When a second phenyl was introduced in [$^{11}$C]-4, not only did the biodistribution parameters surpass those of the other tracers, but washout from the myocardium became negligible and thus heart/tissue ratios improved over time. It is therefore evident that all three factors affect the biodistribution of the ammonium salt tracers. The most important factor, by far, was found to be the distribution of lipophilicity around the cationic core. Even though [$^{11}$C]-4's C Log P is lower than that of [$^{11}$C]-7's, it gave the highest cardiac uptake with negligible washout and improved heart/tissue ratios at later time points.

In light of these results, the distribution of [$^{11}$C]-4 was evaluated in rats. Similarly to the results obtained with mice, a rapid accumulation of radioactivity was observed in the heart, reaching stable heart SUVs of about 15. Moreover, since radioactivity uptake levels were significantly lower in the lungs, kidneys and the liver, remarkable heart/tissue uptake ratios of 2.4, 3.5 and 3.2 were calculated at 10 min after injection, respectively (FIG. 5). Importantly, due to the high clearance of radioactivity from blood, heart/blood activity ratios ranged from 67.5-88.5 at 5-15 min after injection of [$^{11}$C]-4, respectively. Altogether, these results suggest that the myocardial uptake of [$^{11}$C]-4 is high and stable, with a significant signal/noise ratio, as would be expected from a MPI agent.

MicroPET studies in rats reinforced the aforementioned biodistribution results. Specifically, rapid and significant myocardial uptake of [$^{11}$C]-4 was observed within few minutes after injection. When compared to the referenced prevailing MPI PET probe, [$^{13}$N]NH$_3$, image quality was better following [$^{11}$C]-4 injection. Two important issues should be addressed in this regard: (i) The % ID/mL values measured in the microPET studies were inconsistent with those obtained from the biosidtribution studies at the same time points. (ii) A moderate, but consistent increase of radioactivity levels in the myocardium was observed in the microPET. The inconsistencies in measured radioactivity concentrations between the two studies could most likely be attributed to the fact that rats were under isoflurane anesthesia during the microPET studies, whereas no anesthesia was applied during the biodistribution experiments. As for the second observation, and since the mild elevation of myocardial radioactivity uptake parallels the continuous reduction of activity levels in the liver, one could not rule out the possible accumulation of radioactive metabolites in the myocardium at later time points. These observations warrant further in-depth investigations.

In addition to the above observations in small animals, we have similarly shown in this study that [$^{11}$C]-4 accumulates rapidly in the porcine myocardium to high levels, while simultaneously, blood pool and lung activities rapidly clear off. Remarkably, both left ventricular and right ventricular walls are clearly visualized with high target to non-target ratio between the myocardium and heart cavities, respectively. Considerable right ventricular uptake has been shown recently with new fluorine-18 labeled MPI tracers, but is usually less pronounced with traditional PET MPI tracers such as [$^{13}$N]NH$_3$. In addition, no net washout of [$^{11}$C]-4 from the myocardium was observed throughout the dynamic acquisition, suggesting that tracer injection away from the camera (e.g., during a treadmill exercise) with PET data collection performed approximately 10 min later is feasible. A point of concern with the [$^{11}$C]-4 tracer is its significant liver uptake occasionally surpassing that of the myocardium. Liver uptake could potentially interfere with cardiac imaging via radioactivity scatter and through reconstruction artifacts. However, due to better spatial resolution, these problems should not be as significant in PET as they are sometimes in SPECT imaging. Indeed, we encountered no overt imaging problems with our studies that could have been attributed to liver uptake. In addition, inter-species biological variability and also human individual variability of liver uptake can be reasonably anticipated for [$^{11}$C]-4.

Myocardial images of high quality are certainly desirable for an MPI tracer, yet, above all, its "sine qua non" trademark is identified with the ability to diagnose significant coronary stenosis. Therefore, a good MPI tracer must show the so-called "reversible ischemia" imaging pattern, i.e., a perfusion defect created on stress images that fills-in on rest images. Awareness of this indispensable and essential characteristic of any MPI tracer motivated us to create a novel model for reversible coronary ischemia in swine using a stent wherein its expansion was associated with significant coronary stenosis. Only in the third pig we succeeded in preventing complete obstruction of the artery throughout the experiment, as was evident on coronary angiography performed immediately after stent insertion and additionally at the end of the day. Indeed, FIG. 8 shows in that case a severe defect in the inferolateral left ventricular wall on data acquired with [$^{11}$C]-4 during adenosine stress, while no significant defect is noted in the same area, on rest injection. [$^{13}$N]NH$_3$ images collected during similar pharmacological stress show comparable stress defect to [$^{11}$C]-4 images (FIG. 11).

Attempts with stent insertion in pigs 1 and 2 resulted in total coronary artery occlusion as was evident on repeated angiography and by early development of ST-elevation myocardial infarction on ECG monitoring, respectively. The corresponding images show patterns that are compatible with what is considered clinically to be representative of myocardial infarction—a very severe, fixed, inferior wall defect in the case of pig 1 and a severe, fixed, inferior wall defect, with partial inferolateral wall reversibility in the case of pig 2.

The following are the various embodiments of the invention:

A radiolabeled compound of Formula (I):

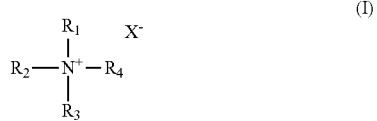

(I)

wherein
each of $R_1$, $R_2$, $R_3$ and $R_4$, independently of each other is selected from $C_1$-$C_{10}$ alkyl, $C_2$-$C_{10}$alkenyl, $C_2$-$C_{10}$alkynyl, $C_3$-$C_{10}$cycloalkyl, $C_6$-$C_{18}$aryl, $C_5$-$C_{18}$heteroaryl, $C_1$-$C_{10}$aralkyl, polyethylenglycol, $C_1$-$C_6$alkyl-O—CH$_2$—(CH$_2$—O—CH$_2$)$_n$—CH$_2$—OH and $C_1$-$C_6$alkyl-(O—CH$_2$—CH$_2$)$_m$—OH;

at least one of $R_1$, $R_2$, $R_3$ and $R_4$ is or comprises at least radiolabeled atom or substituent;

each of n and m, independently of each other is an integer between 2 and 10; and X is a negatively charged pharmaceutically acceptable ion.

The compound may be one wherein each of $R_1$, $R_2$, $R_3$ and $R_4$, independently of the other, is optionally substituted by one or more substituent selected from $C_1$-$C_6$alkyl, $C_6$-$C_{18}$aryl, halide (Cl, Br, I, F), nitro, amine, hydroxyl, ether and a chelating agent.

The compound may be one wherein the alkyl group is said $C_1$-$C_{10}$alkyl or $C_1$-$C_{10}$aralkyl has 1, 2, or 3 carbon atoms, one of which carbon atoms being substituted by one or more F atoms.

The compound may be one wherein the alkyl group has 1 or 2 carbon atoms, one of which carbon atoms being substituted by one or more F atoms.

The compound may be one wherein the alkyl group is polyethylenglycol (PEG), one of the ethylene carbons may be substituted by an F atom.

The compound may be one wherein at least one of $R_1$, $R_2$ and $R_3$ is a $C_1$-$C_{10}$alkyl.

The compound may be one wherein at least two of $R_1$, $R_2$ and $R_3$ is a $C_1$-$C_{10}$alkyl.

The compound may be one wherein each of $R_1$, $R_2$ and $R_3$ is a $C_1$-$C_8$alkyl.

The compound may be one wherein $R_4$ is a radiolabeled $C_1$-$C_8$alkyl.

The compound may be one wherein at least one of $R_1$, $R_2$ and $R_3$ is a $C_1$-$C_{10}$alkyl and $R_4$ is a $C_6$-$C_{18}$aryl.

The compound may be one wherein two of $R_1$, $R_2$ and $R_3$ are each, independently, a $C_1$-$C_{10}$alkyl and the other of $R_1$, $R_2$ and $R_3$ is a $C_6$-$C_{18}$aryl, and $R_4$ is a $C_6$-$C_{18}$aryl.

The compound may be one wherein each of $R_1$ and $R_2$, independently, is a $C_1$-$C_{10}$alkyl and each of $R_3$ and $R_4$, independently, is a $C_6$-$C_{18}$aryl.

The compound may be one wherein at least one of $R_1$, $R_2$ and $R_3$ is a $C_6$-$C_{18}$aryl, being optionally substituted.

The compound may be one wherein at least one of $R_1$, $R_2$ and $R_3$ is a $C_6$-$C_{18}$aryl, being optionally substituted, and $R_4$ is a $C_1$-$C_{10}$alkyl.

The compound may be one wherein each of $R_1$, $R_2$, $R_3$ and $R_4$, independently of each other, is an optionally substituted $C_1$-$C_{10}$alkyl.

The compound may be one wherein at least one of said $R_1$, $R_2$, $R_3$ and $R_4$ is a $C_1$-$C_{10}$alkyl being different from a methyl, and at least one of said $R_1$, $R_2$, $R_3$ and $R_4$ is a methyl group.

The compound may be one wherein each of $R_1$, $R_2$, $R_3$ and $R_4$ is a methyl group, at least one which being radiolabeled.

The compound is Compound [$^{11}$C]-1.

The compound may be one wherein two of $R_1$, $R_2$, $R_3$ and $R_4$, independently of each other, is an optionally substituted $C_1$-$C_{10}$alkyl and the other two of $R_1$, $R_2$, $R_3$ and $R_4$, independently of the other, is an optionally substituted $C_6$-$C_{18}$aryl.

The compound may be one wherein three of $R_1$, $R_2$, $R_3$ and $R_4$, independently of each other, is an optionally substituted $C_1$-$C_{10}$alkyl and the other one of $R_1$, $R_2$, $R_3$ and $R_4$ is an optionally substituted $C_6$-$C_{18}$aryl.

The compound may be one wherein $R_1$ is a $C_6$-$C_{18}$aryl.

The compound may be one wherein said aryl being a substituted or unsubstituted phenyl ring.

The compound being a compound of Formula (II):

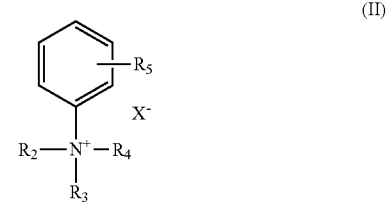

(II)

wherein
each of $R_2$, $R_3$ and $R_4$, independently of each other is selected from $C_1$-$C_{10}$ alkyl, $C_2$-$C_{10}$alkenyl, $C_2$-$C_{10}$alkynyl, $C_3$-$C_{10}$cycloalkyl, $C_6$-$C_{18}$aryl, $C_5$-$C_{18}$heteroaryl, $C_1$-$C_{10}$aralkyl, polyethylenglycol, $C_1$-$C_6$alkyl-O—CH$_2$—(CH$_2$—O—CH$_2$)$_n$—CH$_2$—OH and $C_1$-$C_6$alkyl-(O—CH$_2$—CH$_2$)$_m$OH;

at least one of $R_2$, $R_3$ and $R_4$ is or comprises at least radiolabeled atom or substituent;

$R_5$ is one or two or three or four or five substitutions on the ring, the substituting group being selected from —H, halide (i.e., Cl, Br, I, F), nitro (—$NO_2$), amine (—$NH_2$, —NH—$C_1$-$C_6$alkyl, —N($C_1$-$C_6$alkyl)$_2$), hydroxyl (—OH), $C_1$-$C_6$alkyl, $C_2$-$C_6$alkenyl, $C_2$-$C_6$alkynyl, $C_3$-$C_6$cycloalkyl, $C_1$-$C_6$alkoxy (—O—$C_1$-$C_6$alkyl), $C_6$-$C_{18}$aryl, $C_5$-$C_{10}$heteroaryl, $C_1$-$C_{10}$aralkyl, polyethylenglycol, $C_1$-$C_6$alkyl-O—$CH_2$—($CH_2$—O—$CH_2$)$_z$—$CH_2$—OH and $C_1$-$C_6$alkyl-(O—$CH_2$—$CH_2$)$_y$—OH;

each of n and m, independently of each other is an integer between 2 and 10;

each of z and y, independently of each other is an integer between 2 and 10; and X is a negatively charged pharmaceutically acceptable ion.

The compound may be one wherein each of $R_2$, $R_3$ and $R_4$ is a $C_1$-$C_{10}$alkyl, at least one of said $R_2$, $R_3$ and $R_4$ comprising at least one radiolabeled atom or substituent.

The compound may be one wherein each of $R_2$, $R_3$ and $R_4$, independently of the other is a radiolabeled methyl or an ethyl.

The compound may be one wherein each of $R_2$, $R_3$ and $R_4$ is a methyl, one of said methyl groups being radiolabeled.

The compound is Compound [$^{11}$C]-2.

The compound may be one wherein $R_5$ is one or more substituents, each being independently selected from halide, nitro, amine, hydroxyl, $C_1$-$C_{10}$alkyl, $C_2$-$C_6$alkenyl, $C_2$-$C_6$alkynyl, $C_3$-$C_6$cycloalkyl, $C_1$-$C_{10}$alkoxy (—O—$C_1$-$C_{10}$alkyl), $C_6$-$C_{18}$aryl, $C_5$-$C_{10}$heteroaryl, $C_1$-$C_{10}$aralkyl, polyethylenglycol, $C_1$-$C_6$alkyl-O—$CH_2$—($CH_2$—O—$CH_2$)$_z$—$CH_2$—OH and $C_1$-$C_6$alkyl-(O—$CH_2$—$CH_2$)$_y$—OH.

The compound may be one wherein $R_5$ is a single substituent at any position of the phenyl ring.

The compound may be one wherein $R_5$ is a single substituent at the ortho position.

The compound may be one wherein $R_5$ is a single substituent at the meta position.

The compound may be one wherein $R_5$ is a single substituent at the para position.

The compound may be one wherein $R_5$ is a halide, an amine, an hydroxyl, or a $C_1$-$C_{10}$alkyl.

The compound may be one wherein $R_5$ is —$NH_2$.

The compound may be one wherein $R_5$ is —N($C_1$-$C_{10}$alkyl)$_2$, wherein each of the two $C_1$-$C_{10}$alkyl groups is same or different.

The compound may be one wherein the two $C_1$-$C_{10}$alkyl groups are the same, being selected from methyl and ethyl.

The compound may be one wherein each of the two groups is a methyl.

The compound is Compound [$^{11}$C]-3.

The compound may be one wherein $R_5$ is a $C_1$-$C_{10}$alkyl.

The compound may be one wherein the $C_1$-$C_{10}$alkyl is selected from methyl, ethyl, propyl, iso-propyl and n-butyl.

The compound may be one wherein $C_1$-$C_{10}$alkyl is a methyl group.

The compound is Compound [$^{11}$C]-6.

The compound may be one wherein $R_1$ is a $C_6$-$C_{18}$aryl, said aryl being different from a phenyl.

The compound may be one wherein the $C_6$-$C_{18}$aryl is naphthyl and the compound is of Formula (III):

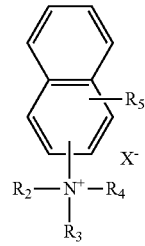

(III)

wherein the naphthyl moiety may be bonded to the N atom of the quaternary ammonium group via any of the naphthyl carbon atoms, and wherein each of $R_2$, $R_3$ and $R_4$, independently of each other is selected from $C_1$-$C_{10}$ alkyl, $C_2$-$C_{10}$alkenyl, $C_2$-$C_{10}$alkynyl, $C_3$-$C_{10}$cycloalkyl, $C_6$-$C_{18}$aryl, $C_5$-$C_{18}$heteroaryl, $C_1$-$C_{10}$aralkyl, polyethylenglycol, $C_1$-$C_6$alkyl-O—$CH_2$—($CH_2$—O—$CH_2$)$_n$—$CH_2$—OH and $C_1$-$C_6$alkyl-(O—$CH_2$—$CH_2$)$_m$—OH;

at least one of $R_2$, $R_3$ and $R_4$ is or comprises at least radiolabeled atom or substituent;

$R_5$ is one or two or three or four or five or six or seven substitutions on the naphthyl ring, the substituting group being selected from —H, halide (i.e., Cl, Br, I, F), nitro (—$NO_2$), amine (—$NH_2$, —NH—$C_1$-$C_{10}$alkyl, —N($C_1$-$C_{10}$alkyl)$_2$), hydroxyl (—OH), $C_1$-$C_{10}$alkyl, $C_2$-$C_6$alkenyl, $C_2$-$C_6$alkynyl, $C_3$-$C_6$cycloalkyl, $C_1$-$C_{10}$alkoxy (—O—$C_1$-$C_{10}$alkyl), $C_6$-$C_{10}$aryl, $C_5$-$C_{10}$heteroaryl, $C_1$-$C_{10}$aralkyl, polyethylenglycol, $C_1$-$C_6$alkyl-O—$CH_2$—($CH_2$—O—$CH_2$)$_z$—$CH_2$—OH and $C_1$-$C_6$alkyl-(O—$CH_2$—$CH_2$)$_y$—OH;

each of n and m, independently of each other is an integer between 2 and 10;

each of z and y, independently of each other is an integer between 2 and 10; and X is a negatively charged pharmaceutically acceptable ion.

The compound may be one wherein the compound is of the Formula (IV):

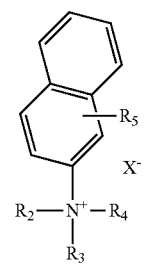

(IV)

The compound may be one wherein $R_5$ is —H.

The compound may be one wherein each of $R_2$, $R_3$ and $R_4$ is a $C_1$-$C_{10}$alkyl, at least one of said $R_2$, $R_3$ and $R_4$ comprising at least one radiolabeled atom or substituent.

The compound may be one wherein each of $R_2$, $R_3$ and $R_4$, independently of the other is a radiolabeled $C_1$-$C_{10}$alkyl selected from a methyl, ethyl, propyl, iso-propyl and n-butyl.

The compound may be one wherein each of $R_2$, $R_3$ and $R_4$, independently of the other is a radiolabeled methyl or an ethyl.

The compound may be one wherein each of $R_2$, $R_3$ and $R_4$ is a methyl, one of said methyl groups being radiolabeled.

The compound is Compound [$^{11}$C]-7.

The compound may be one wherein each of $R_1$ and $R_2$ is a $C_6$-$C_{18}$aryl.

The compound may be one wherein said aryl is a substituted or unsubstituted phenyl ring.

The compound may be one wherein the compound is of Formula (V):

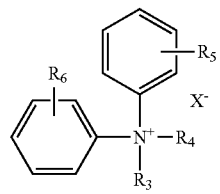

(V)

wherein each of $R_3$ and $R_4$, independently of the other is selected from $C_1$-$C_{10}$ alkyl, $C_2$-$C_{10}$alkenyl, $C_2$-$C_{10}$alkynyl, $C_3$-$C_{10}$cycloalkyl, $C_6$-$C_{18}$aryl, $C_5$-$C_{18}$heteroaryl, $C_1$-$C_{10}$aralkyl, polyethylenglycol, $C_1$-$C_6$alkyl-O—CH$_2$—(CH$_2$—O—CH$_2$)$_6$—CH$_2$—OH and $C_1$-$C_6$alkyl-(O—CH$_2$—CH$_2$)$_m$—OH; at least one of $R_3$ and $R_4$ is or comprises at least radiolabeled atom or substituent;

each of $R_5$ and $R_6$, independently of the other, is one or two or three or four or five substitutions on the respective rings (as detailed hereinabove), the substituting group being selected from —H, halide (i.e., Cl, Br, I, F), nitro (—NO$_2$), amine (—NH$_2$, —NH—$C_1$-$C_{10}$alkyl, —N($C_1$-$C_{10}$alkyl)$_2$), hydroxyl (—OH), $C_1$-$C_{10}$alkyl, $C_2$-$C_6$alkenyl, $C_2$-$C_6$alkynyl, $C_3$-$C_6$cycloalkyl, $C_1$-$C_{10}$alkoxy (—O—$C_1$-$C_{10}$alkyl), $C_6$-$C_{18}$aryl, $C_5$-$C_{10}$heteroaryl, $C_1$-$C_{10}$aralkyl, polyethylenglycol, $C_1$-$C_6$alkyl-O—CH$_2$—(CH$_2$—O—CH$_2$)$_z$—CH$_2$—OH and $C_1$-$C_6$alkyl-(O—CH$_2$—CH$_2$)$_y$—OH;

each of n and m, independently of each other is an integer between 2 and 10;

each of z and y, independently of each other is an integer between 2 and 10; and X is a negatively charged pharmaceutically acceptable ion (anion).

The compound may be one wherein each of $R_3$ and $R_4$ is a $C_1$-$C_{10}$alkyl, at least one of said $R_3$ and $R_4$ comprising at least one radiolabeled atom or substituent.

The compound may be one wherein at least one of the substituting $R_5$, and/or $R_6$, representing a single substituting or multiple substituting groups is —H or a $C_1$-$C_{10}$alkyl.

The compound may be one wherein each of $R_5$ and/or $R_6$ is —H, each of $R_3$ and $R_4$, independently of the other is a radiolabeled $C_1$-$C_{10}$ alkyl selected from a methyl, ethyl, propyl, iso-propyl and n-butyl.

The compound may be one wherein each of $R_3$ and $R_4$, independently of the other is a radiolabeled methyl or an ethyl.

The compound may be one wherein each of $R_3$ and $R_4$ is a methyl, one of said methyl groups being radiolabeled.

The compound is Compound [$^{11}$C]-4.

The compound may be one wherein at least one of $R_3$ and $R_4$ is not a methyl group.

The compound may be one wherein at least one of $R_3$ and $R_4$ is an ethyl group and the other of $R_3$ and $R_4$ is a methyl group.

The compound may be one wherein one of said $R_3$ and $R_4$ is optionally substituted.

The compound is Compound [$^{18}$F]-5.

The compound may be one wherein X is an anion derived from an inorganic acid or from an organic acid.

The compound may be one wherein X is derived from an inorganic acid.

The compound may be one wherein X is selected from sulfate, pyrosulfate, bisulfate, sulfite, bisulfate, nitrate, phosphate, monohydrogenphosphate, dihydrogenphosphate, metaphosphate, pyrophosphate, chloride, bromide, iodide, acetate, propionate, caprylate, isobutyrate, oxalate, malonate, succinate, suberate, sebacate, fumarate, maleate, mandelate, benzoate, chlorobenzoate, methylbenzoate, dinitrobenzoate, phthalate, benzenesulfonate, toluenesulfonate, phenylacetate, citrate, lactate, maleate, tartrate, trifluoromethanesulfonate and methanesulfonate.

The compound may be one wherein X is selected from iodide, benzenesulfonate, toluenesulfonate, trifluoromethanesulfonate and methanesulfonate.

The compound may be one wherein X is selected from iodide and trifluoromethanesulfonate.

The compound may be one wherein the radiolabeled atom is selected from $^{18}$F, $^{15}$O, $^{13}$N, and $^{11}$C.

The compound may be one wherein the radiolabeled atom is $^{11}$C.

The compound may be one wherein the radiolabeled atom is $^{18}$F.

The compound may be one wherein the radiolabeled atom is $^{13}$N.

The compound may be one wherein the radiolabeled atom is not $^{18}$F.

A compound selected from:

[$^{11}$C]tetramethyl-ammonium iodide,

[$^{11}$C]trimethyl-phenyl-ammonium iodide,

[$^{11}$C](4-dimethylamino-phenyl)-trimethyl-ammonium iodide,

[$^{11}$C]dimethyl-diphenyl-ammonium iodide,

2-[$^{18}$F]fluoro-ethyl)-methyl-diphenyl-ammonium trifluoromethanesulfonate,

[$^{11}$C]Methyl-dimethyl-m-tolyl-ammonium iodide,

[$^{11}$C]Methyl-dimethyl-1-naphtylammonium trifluoromethanesulfonate.

A radiopharmaceutical being or comprising a compound of the invention.

The radiopharmaceutical may be in the form of an aqueous solution.

The radiopharmaceutical may be in the form of a formulation optionally further comprising at least one additive.

The radiopharmaceutical may be one wherein said additive is selected from a pH-adjusting agent, a pharmaceutically acceptable stabilizer, an antioxidant, an antimicrobial preservative, an organic solvent and a filler.

The compound or the radiopharmaceutical according to the invention for use in medicine.

The radiopharmaceutical for use in the diagnosis of a disease or disorder.

The radiopharmaceutical for use in risk stratification.

The radiopharmaceutical may be one wherein the disease or disorder is selected from a cardiac disease, renal, neuronal and neoplastic diseases or disorders.

Use of at least one compound according to the invention for the preparation of a composition.

The use may be one wherein said composition is a pharmaceutical composition or a radiopharmaceutical or a diagnostic composition.

The use may be one wherein the diagnostic composition is suitable for use as a biomarker for diagnosis of a disease and disorder in a human and non-human subject using molecular imaging.

The use may be one wherein the molecular imaging is a non-invasive molecular imaging technique.

The use may be one wherein the non-invasive molecular imaging technique is selected from myocardial perfusion imaging (MPI), Positron Emission Tomography (PET) and Single Photon Emission Computed Tomography (SPECT).

The use may be one wherein the molecular imaging technique is PET.

A diagnostic composition comprising at least one compound according to the invention for use in the diagnosis of a disease or disorder.

The diagnostic composition may be used alongside tracers radiolabeled with a different tracer than the one used in the diagnostic composition.

The diagnostic composition may be one wherein disease or disorder is a cardiac disease, for use in one or more of:
(i) in the prognosis and risk stratification of cardiac disease in patients with known or suspected cardiac disease;
(ii) in the prediction of functional recovery following acute myocardial infarction;
(iii) in the prediction of functional recovery after revascularization in patients with chronic ischemic left ventricle (LV) dysfunction; and
(iv) in determining blood flow to the heart muscle, for determining the effects of a heart attack, or myocardial infarction, on areas of the heart, to identify areas of the heart muscle that would benefit from a procedure or to map normal heart function.

A method for the diagnosis of a disease or disorder, said method comprising administering to a subject suffering from or having predisposition to suffer from or having symptoms which may be associated with the disease or disorder, a diagnostically effective amount of a compound of the invention or a radiopharmaceutical or a diagnostic composition comprising same, and imaging the body or any part of the body of said subject.

The method may be one wherein the disease or disorder is coronary artery disease.

A method of monitoring treatment of a subject, said method comprising administering to a subject having a disease or disorder a compound as defined herein or a radiopharmaceutical, as defined herein, or a diagnostic composition according to the invention and measuring at least one imaging parameter associated with the disease or disorder in the subject using imaging of the body or any part of the body of said subject.

The method may be one wherein the imaging technique is MPI, PET or SPECT.

A method for determining the severity of a disease or disorder, in a subject, the method comprising:
(i) obtaining at least one imaging parameter following the administration of at least one compound according to the invention or at least one radiopharmaceutical or at least one composition comprising same to a subject suffering from the disease or disorder,
(ii) comparing the at least one imaging parameter obtained in (i) with a control reference that correlates with the severity of the disease or disorder, wherein the comparison allowing the determination of the severity of the disease or disorder in the subject.

A method for determining the effectiveness of a therapeutic treatment of a disease or disorder in a subject, said method comprising:
(i) obtaining at least one imaging parameter following the administration, at a first time point, at least one compound according to the invention or at least one radiopharmaceutical or at least one composition comprising same to the subject suffering from the disease or disorder,
(ii) comparing the at least one imaging parameter obtained in (i) with at least one imaging input parameter obtained, following the administration, at a second time point, of at least one radiolabeled compound or at least one radiopharmaceutical or at least one composition to the subject suffering from the disease or disorder, and wherein the comparison allowing the determination of the effectiveness of a therapeutic treatment.

The invention claimed is:

1. A radiolabeled compound selected from the group consisting of
   [$^{11}$C]trimethyl-phenyl-ammonium iodide,
   [$^{11}$C]dimethyl-diphenyl-ammonium iodide,
   2-[$^{18}$F]fluoro-ethyl)-methyl-diphenyl-ammonium trifluoromethanesulfonate, and
   [$^{11}$C]Methyl-dimethyl-1-naphtylammonium trifluoromethanesulfonate.

2. A pharmaceutical composition comprising the radiolabeled compound according to claim 1.